(12) United States Patent
Kuhn

(10) Patent No.: US 11,300,495 B2
(45) Date of Patent: Apr. 12, 2022

(54) FLOW CYTOMETER ARRANGEMENT

(71) Applicant: Martin Kuhn, Glattfelden (CH)

(72) Inventor: Martin Kuhn, Glattfelden (CH)

(73) Assignee: Martin Kuhn, Glattfelden (CH)

( * ) Notice: Subject to any disclaimer, the term of this patent is extended or adjusted under 35 U.S.C. 154(b) by 125 days.

(21) Appl. No.: 16/767,467

(22) PCT Filed: Nov. 27, 2018

(86) PCT No.: PCT/EP2018/082712
§ 371 (c)(1),
(2) Date: May 27, 2020

(87) PCT Pub. No.: WO2019/102038
PCT Pub. Date: May 31, 2019

(65) Prior Publication Data
US 2020/0371013 A1   Nov. 26, 2020

(30) Foreign Application Priority Data
Nov. 27, 2017 (DE) .......................... 102017128029.4

(51) Int. Cl.
*G01N 1/14* (2006.01)
*G01N 15/14* (2006.01)
(Continued)

(52) U.S. Cl.
CPC .......... *G01N 15/1434* (2013.01); *G01N 1/14* (2013.01); *G01N 1/31* (2013.01); *G01N 1/38* (2013.01); *G01N 15/1404* (2013.01); *G01N 33/18* (2013.01); *G01N 2015/0088* (2013.01); *G01N 2015/1006* (2013.01); *G01N 2015/1409* (2013.01); *G01N 2015/1413* (2013.01); *G01N 2015/1486* (2013.01)

(58) Field of Classification Search
CPC ........ G01N 15/1434; G01N 1/14; G01N 1/31; G01N 1/38; G01N 15/1404; G01N 33/18; G01N 2015/0088; G01N 2015/1006; G01N 2015/1409; G01N 2015/1413; G01N 2015/1486
See application file for complete search history.

(56) References Cited

U.S. PATENT DOCUMENTS

| | | | | |
|---|---|---|---|---|
| 4,695,431 A | * | 9/1987 | Farrell | G01N 35/1095 417/267 |
| 5,978,435 A | * | 11/1999 | Christensen | G01N 15/1456 377/10 |

(Continued)

FOREIGN PATENT DOCUMENTS

| | | |
|---|---|---|
| EP | 0634640 A1 | 1/1995 |
| WO | 9707390 A1 | 2/1997 |

OTHER PUBLICATIONS

International Preliminary Report on Patentability for International Application No. PCT/EP2018/082712 dated Jun. 2, 2020 (7 pages).

(Continued)

*Primary Examiner* — Roy M Punnoose
(74) *Attorney, Agent, or Firm* — Reising Ethington, P.C.

(57) ABSTRACT

The disclosure relates to a flow cytometer arrangement, in which a sample is mixed with a colorant by means of two pumps and the mixture is introduced together with a sheath flow into a flow cell.

10 Claims, 21 Drawing Sheets

(51) Int. Cl.
*G01N 1/31* (2006.01)
*G01N 1/38* (2006.01)
G01N 33/18 (2006.01)
G01N 15/00 (2006.01)
G01N 15/10 (2006.01)

(56) References Cited

U.S. PATENT DOCUMENTS

| | | | | |
|---|---|---|---|---|
| 6,157,692 | A * | 12/2000 | Christensen | G01N 15/1456 |
| | | | | 377/10 |
| 6,884,231 | B1 * | 4/2005 | Walters | B01L 3/0217 |
| | | | | 604/131 |
| 2014/0087389 | A1 * | 3/2014 | Heller | G01N 21/6486 |
| | | | | 435/6.15 |
| 2020/0319078 | A1 * | 10/2020 | Shi | B01F 13/0059 |

OTHER PUBLICATIONS

English Translation of International Preliminary Report on Patentability for International Application No. PCT/EP2018/082712 dated Jun. 2, 2020 (5 pages).
International Search Report for International Application No. PCT/EP2018/082712 dated Apr. 10, 2019, 3 pages.
English Translation of International Search Report for International Application No. PCT/EP2018/082712 dated Apr. 10, 2019, 2 pages.

* cited by examiner

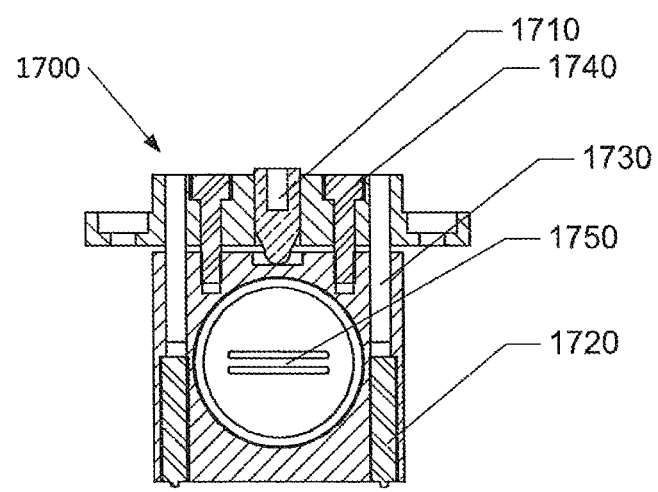
Section A-A
Fig. 4
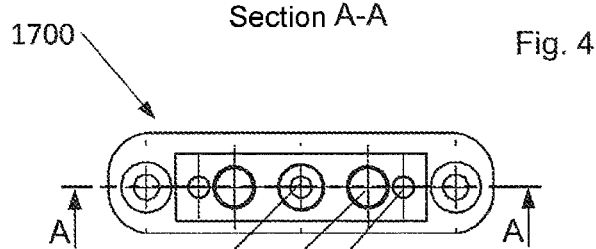
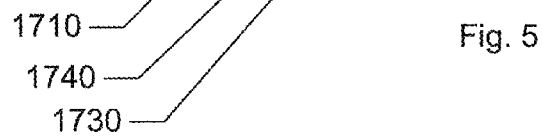
Fig. 5

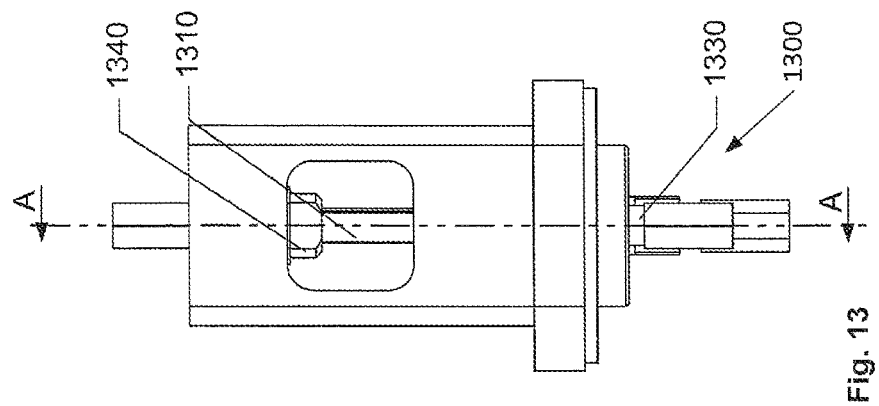
Fig. 13
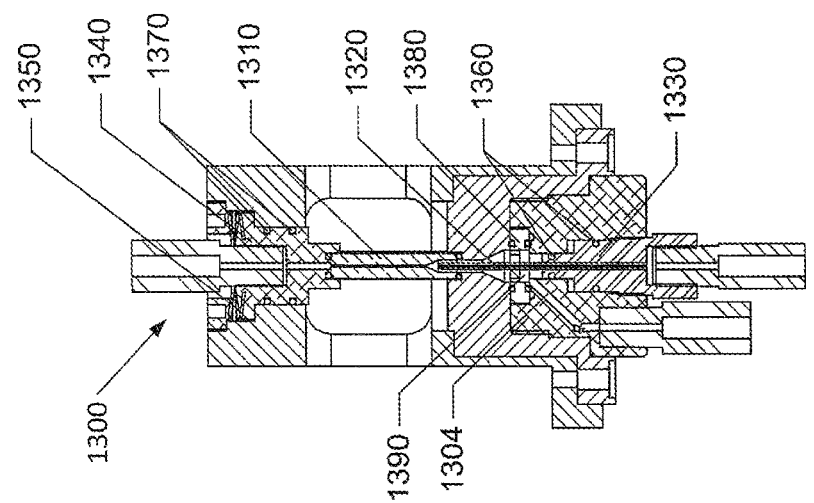
Fig. 12  Section A-A

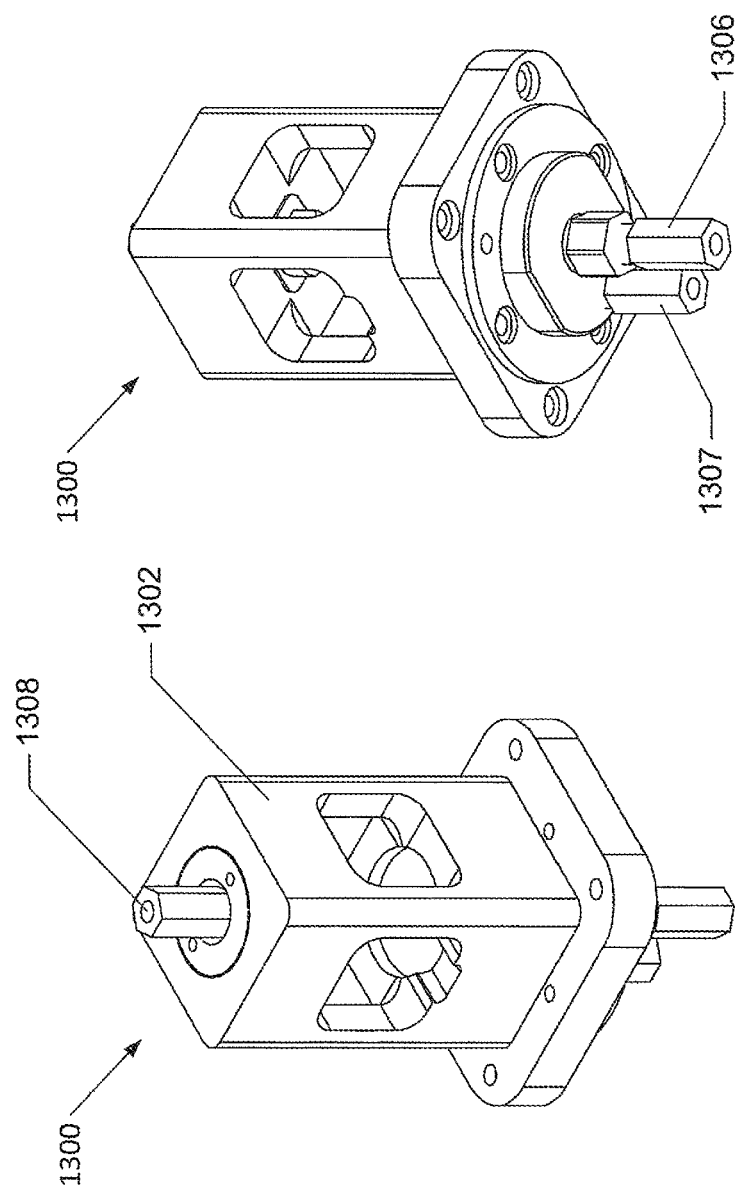

FLOW CYTOMETER ARRANGEMENT

INTRODUCTION

The disclosure relates to a flow cytometer arrangement.

The hygiene state of drinking water has been ascertained for more than 100 years by what is called the AMK method (AMK=aerobic mesophilic bacteria). This typically involves applying water samples to a culture medium and incubating over 72 hours, for example. Thereafter, the colonies that may have formed are counted, which permits a conclusion as to the number of colony-forming units (CFU) present in the drinking water.

This conventional method is very inexact, in that it detects merely the aerobic mesophilic bacteria. It is additionally time-consuming and can only be performed in specialist laboratories for this purpose.

Drinking water is nowadays subject to ever greater influences, for example rising temperature, extreme weather situations or burdens resulting from agriculture and industry. In order to be able to take measures immediately in the case of a relevant event, new technologies for real-time determination of the microbiological situation are required.

It is already possible to monitor sediments and organic and inorganic parameters in drinking water online. However, there has to date been a lack of technology for measurement of microbiological parameters on site.

The number of aerobic mesophilic bacteria (AMK) that has already been mentioned above is nowadays regarded as a measure of microbial contamination of a foodstuff by bacteria, yeasts and molds. Incubation of the water sample already mentioned on culture medium results in growth of aerobic mesophilic bacteria, if present, into colonies.

However, it has been found that this method covers only a small portion of about 0.01% to 1% of the microorganisms present in the water. The AMK tolerance values of 20 CFU/ml in the treated drinking water and 300 CFU/ml in the distribution network that are laid down in the Swiss Hygieneverordnung [Hygiene Act] in no way represent the active cells that are actually present.

Apart from the disadvantages already mentioned, such as the ascertained cell count which is too small by a considerable degree and the very slow procedure that takes 48 to 72 hours, for example, it should also be noted that tolerances and limits vary according to the culture medium and incubation technology.

It cannot be assumed that there is a correlation between AMK and total cell count since the proportion of cultivatable cells varies significantly.

In order to ascertain the actual number of cells in the drinking water, it has already been suggested that flow cytometry be used. This typically involves mixing water samples with dyes that bind to the DNA or RNA of bacteria and hence render them visible. The bacteria labeled in this way can then be detected and counted individually, for example by excitation by means of a laser beam.

In the case of drinking water from the city of Zürich, the AMK method mentioned further up gives, for example, between 0 and 10 cells per milliliter. By flow cytometry, by contrast, a total cell count between 80 000 and 10 000 cells per milliliter is ascertained. Such large numbers require a rethink, both on the part of the water supplier and on the part of the consumer. In environmental water samples, the proportion of intact cells is usually about 80% to 90%, as demonstrated by a multitude of microscopy studies. It can be assumed that a determination of the total cell count by means of flow cytometry can reliably determine the actual number of microorganisms in drinking water.

However, nothing about the microbiological water quality has changed if distinctly higher cell counts are determined by flow cytometry.

Flow cytometry has been known from medical technology for about 50 years. In hospitals and medical laboratories, its uses include those in hematology, infectology and immunology for routine diagnostics. Further important fields of use are fundamental medical and cell biology research, and the quantitative analysis of cells in biology. Flow cytometers can also count total cell count (TCC), the ratio of HNA (high nucleic acid) and LNA (low nucleic acid), and of living and dead cells. The microorganisms and particles here, after staining and incubating, are flushed individually through a glass capillary and illuminated with a focused laser beam in order to excite the DNA dye. If the laser hits a cell or a particle, the scattered light is detected in the scattered light channel and the light emitted by the cells is detected via the fluorescence channels.

The method of flow cytometry has to date been known essentially from different fields of medicine. It is a fundamental assumption that the method is conducted in a laboratory by trained personnel. For this purpose, a sample has to be supplied manually. Moreover, the instruments available on the market are specified for laboratory conditions, and they are therefore sensitive, for example, to environmental influences such as air humidity and temperature. Fluid vessels for various operating fluids are typically not monitored with sensors, but are merely checked visually. The operation of such systems is not possible continuously. Moreover, there are no electrical interfaces to communicate with further instruments or systems. Known flow cytometers on the market are thus unsuitable for the monitoring of drinking water in a typical city or communal water supply system since this requires automated operation without constant monitoring by qualified personnel. Moreover, it would be desirable to increase tolerance to environmental influences in order to enable the monitoring of drinking water quality under the typical conditions of such water supply, which are distinctly different from plannable and constant laboratory conditions.

SUMMARY

The disclosure relates to a flow cytometer arrangement. The flow cytometer arrangement comprises a flow measurement cell and a mixer. It comprises a first pump and a second pump. It comprises an inlet connection, a dye reservoir and a sheath fluid reservoir.

The first pump, per an embodiment, is connected on the inlet side to the inlet connection for suction of sample fluid. The second pump is connected on the inlet side to the dye reservoir for suction of dye.

The first pump and the second pump, per an embodiment, are connected on the outlet side to the mixer in order to pump sample fluid and dye into the mixer. The mixer is designed to mix the sample fluid and the dye to give a mixture.

The second pump, per an embodiment, is connected on the inlet side to the mixer for suction of the mixture. This connection may, for example, be direct or indirect. An indirect connection is possible, for example, via an incubator mentioned further down.

The first pump, per an embodiment, is connected on the inlet side to the sheath fluid reservoir for suction of sheath fluid.

The second pump, per an embodiment, is connected on the outlet side to the flow measurement cell in order to produce a sample jet through the flow measurement cell from the mixture. The first pump is connected on the outlet side to the flow measurement cell in order to produce a sheath jet through the flow measurement cell that ensheaths the sample jet from the sheath fluid.

The flow cytometer arrangement of the disclosure, per an embodiment, permits automated performance of flow cytometry, which dispenses with constant manual intervention by trained personnel or even just supervision. The flow cytometer arrangement of the disclosure is designed such that all steps needed for successful measurement of cells in samples can be performed in a fully automated manner. This makes it possible to better address different environmental conditions since automated monitoring is possible if required.

The execution with just two pumps makes the flow cytometer arrangement described very compact.

The sample jet through the flow measurement cell is typically that jet in which the cells to be measured are labeled and present individually, such that they can be measured and/or counted by suitable procedures described further down.

The mixer typically serves to mix sample fluid with dye in order to enable the incorporation of dyes already described above into DNA or RNA of cells. It will be apparent that the dye reservoir and the sheath fluid reservoir may especially be containers that may be part of the flow cytometer arrangement. The dye reservoir and/or the sheath fluid reservoir may, however, also be connections to an external supply with dye and/or sheath fluid.

As mentioned, the sheath fluid generates a sheath jet that typically serves for hydrodynamic focusing of the sample jet. In this way, per an embodiment, the sample jet can be reduced in size, for example, from an original extent of, for example, 90 µm to 110 µm, especially 100 µm, to an extent of, for example, 20 µm to 40 µm, especially 30 µm. The extent is especially based on a diameter of the sample jet in the flow measurement cell. This reduction in size establishes a suitable separation of the cells to be detected.

In one embodiment, the flow cytometer arrangement also comprises a further mixer. This may especially be connected on the inlet side to the first pump and the second pump. The mixer may be connected to the second pump on the outlet side, and this connection may also be a direct or indirect connection, especially via an incubator.

The respective connections between the pumps, i.e. the first pump and the second pump, and the mixers are especially in switchable form, such that the mixer and the further mixer are usable alternatively. This may especially mean that it is possible to define by means of a suitable arrangement of valves whether the first pump and second pump are connected on the outlet side to the mixer or to the further mixer, such that both mixers can be used for corresponding mixing of sample fluid with dye. More particularly, switchability is also possible as to whether the mixer or the further mixer is to supply a respective mixture to the second pump.

Preferably, per an embodiment, a particular mixer is connected here on the outlet side to a particular incubator, which in turn is connected on the outlet side to the second pump. The incubator serves especially to ensure the necessary boundary conditions in order to incorporate the dye reliably into the cells, i.e. to dock it onto DNA or RNA.

It will be apparent that both the mixer and the further mixer, if present, may each be connected to an incubator, in which case it is also possible either for the mixer or the further mixer to be connected to an incubator, or else for there to be no incubator.

A particular incubator, per an embodiment, may especially have a particular heating device in order to heat a mixture released from the mixer into the incubator to a defined temperature for a defined period of time. For example, such an incubator may be designed to heat a mixture to a temperature between 35° C. and 45° C., especially 40° C., for a period of 5 minutes. These are typical boundary conditions for reliable incorporation of dye molecules into cells to be detected, or for docking onto the cells.

In an embodiment, the first pump is designed to suck in a defined first volume of sample fluid from the inlet connection. Further, the second pump is designed to suck in a defined second volume of dye from the dye reservoir. Even further, the first pump and the second pump are designed to pump the first volume of sample fluid and the second volume of dye, after the time of suction, simultaneously into the mixer.

This can ensure batchwise operation, in that sample fluid is first pumped into the first pump and dye into the second pump, and sample fluid and dye are then released into the mixer in a defined manner. The simultaneous release into the mixer ensures particularly good mixing. It is especially also possible to release defined volumes or volume ratios between sample fluid and dye into the mixer. It will be apparent that the mixer may also be the further mixer. This is also true of corresponding occurrences of the term "mixer" in this application.

The pumps may take the form of spindle-actuated piston pumps. This has been found to be useful in practice since the required accuracy in the definition of volumes and pressures can thus be achieved.

In an embodiment, the flow cytometer arrangement comprises a detector arrangement. The detector arrangement in turn comprises a laser designed to generate a laser beam. It also comprises directing optics designed to direct the laser beam toward the flow measurement cell. In addition, it comprises a number of detectors designed to detect a laser beam that has passed through the flow measurement cell.

Such a detector arrangement especially enables fully automated detection with high accuracy of the cells being sought in the sample fluid.

A number is understood to mean a number of one or else more than one. The detector may thus, for example, be one detector, two detectors, three detectors, four detectors or else even more detectors.

The laser may be designed, for example, to generate a laser beam with a wavelength of 488 nm. This has been found to be useful for typical dyes. However, it is also possible to use other wavelengths or spectral regions.

Preferably, per an embodiment, the detector arrangement comprises an at least partly surrounding housing in the form of a tray, in one-piece form. It is also possible to say that the housing is designed as a monoblock. This may mean that the housing has been produced from a single block that has been converted to its final form especially by material-removing methods, for example milling.

This one-piece execution achieves particularly high stability, and it has been found that this generates stability of the components present relative to one another. This ensures reliable measurement even under difficult conditions, for example temperature variations and vibrations. The use of the flow cytometer arrangement outside defined laboratory conditions is thus considerably facilitated, and reliability is increased.

The housing may comprise a number of support projections for components of the detector arrangement. Such support projections may take the form, for example, of elevations in a base of the housing.

The housing may be made into an all-round housing, for example, by means of a lid. Such an all-round housing can, for example, offer complete protection against incidence of light and against the penetration of soiling and/or fluids.

The housing may be formed, for example, from aluminum. However, it is also possible to use other materials, especially other metals.

Preferably, per an embodiment, the detector arrangement comprises a multitude of detectors that detect different spectral regions. For example, it is possible to use four detectors that can correspondingly cover the blue, red, green and yellow spectrum. This has been found to be advantageous, per an embodiment, in practice since it is possible to evaluate spectral regions by means of which the cells being sought can be reliably detected.

It will be apparent that the housing mentioned, executed as a monoblock or in one-piece form, especially of a detector arrangement, can also be regarded as an independent aspect of the disclosure.

In an embodiment, the detector arrangement comprises a double-slit stray light stop, wherein a scattered beam of the laser beam is directed onto a land of the double-slit stray light stop to prevent a signal offset. Such a double-slit stray light stop can also be regarded as an independent aspect of the disclosure.

By means of the double-slit stray light stop, it is possible to suppress the laser beam originally directed onto the sample jet, such that scattered light which is actually caused by cells or particles present in the sample fluid is separated from scattered light that has resulted from pure scatter of the original beam on components of the flow measurement cell, especially of a tube. It is thus also possible to measure the corresponding wavelength of the originally exciting laser and use it for evaluation.

The laser may be a diode laser. This has been found to be advantageous, per an embodiment, for typical applications since it is a reliable and durable design of a laser.

The laser may be part of a laser unit which also comprises an optical fiber for input coupling of the laser beam and an input coupling unit. The input coupling unit may hold an end of the optical fiber facing the laser. This permits simple coupling of the light emitted from the laser into the optical fiber.

The input coupling unit is designed to position a position of the held end of the optical fiber so as to be movable relative to the laser. Movability is possible here in the x-y direction, i.e. in a plane at right angles to the laser beam or at right angles to the extent of the optical fiber. Tilting about one or two axes is also possible. It is also possible to set a focus of the optical fiber in order to enable optimal coupling of the laser beam into the optical fiber.

It should be mentioned that this manner of input coupling may be an independent aspect of the disclosure.

Preferably, per an embodiment, the detector arrangement is configured to detect exclusively scattered light. This has been found to be advantageous in practice. Firstly, by means of the scattered light, detection of cells being sought in the sample fluid is possible. Secondly, by dispensing with detection of transmitted light, a compact design is possible.

Preferably, per an embodiment, the directing optics comprise a focusing element positionable transverse to the laser beam by means of a positioning element and/or rotatable about an optical axis within a tube and/or fixable along its optical axis by means of a threaded plate.

The use of such a focusing element allows the functionalities of multiple components for alignment and focusing of the laser beam to be combined in a single element. It will be apparent that this may be an independent aspect of the disclosure.

In one embodiment, the flow cytometer arrangement comprises a withdrawal unit for withdrawing sample fluid from a fluid stream. The withdrawal unit may be connected to the inlet connection. This enables continuous withdrawal of sample fluid from a fluid stream, for example the fluid stream of a standard communal water supply.

The withdrawal unit may be designed as a crossflow filter. This may be understood to mean an element through which the water jet from which sample fluid is to be taken flows, with a filter directly adjoining said water jet, such that sample fluid can be drawn off from the water jet. The water jet may be defined by a pipe.

The crossflow filter may comprise a channel having an inlet and an outlet. It may also comprise a filter adjoining the channel. The crossflow filter may further comprise a sample outlet connected to the inlet connection for drawing off sample fluid from the channel. This sample outlet is connected to the filter adjoining the channel. This enables direct drawing-off of sample fluid from the water flowing past and the supply of this sample fluid to the inlet connection, where the sample fluid can be analyzed as described.

It will be apparent that the crossflow filter described here may constitute an independent aspect of the disclosure.

The channel may narrow in the region of the filter from the inlet toward the outlet. This continuously increases the flow rate, which prevents bubble formation.

The channel may comprise, per an embodiment, at the inlet, an inlet funnel for distribution of fluid flowing in across the channel. This achieves homogeneous distribution of the fluid flowing in across the channel. In this way too, it is possible to avoid bubble formation.

The outlet may be oblique relative to the channel. This can achieve reliable removal of any bubbles formed. The outlet may be aligned in its installed position such that it is directed obliquely upward. This promotes the removal of bubbles merely by virtue of their tendency to rise upward in water.

The avoidance of bubbles is advantageous, per an embodiment, for flow cytometry since bubbles would severely disrupt the measurement described.

In an embodiment, the flow cytometer arrangement has an individual sample inlet connected to the inlet connection. This enables addition of individual samples for measurement, which constitutes an alternative to continuous withdrawal from water or a water jet flowing past. It will be apparent that both possibilities may be envisaged in a flow cytometer arrangement, meaning that an individual sample inlet and a crossflow filter or another withdrawal unit may be provided. These may then be used as alternatives. For this purpose, for example, suitable valves may be present. However, it is also possible for just one of these two options to be provided, or for there to be another option for supply of a sample.

In an embodiment, the first pump is designed to generate a pressure in the mixer by means of the second pump during suction of the mixture out of the mixer or the incubator, in order to maintain a constant working pressure in the mixer and/or in the incubator. It may also be said, for example, that the pressure is kept constant in spite of the suction of fluid through the second pump out of the mixer or out of the combination and mixer and incubator. This helps to avoid damage to the mixer and/or to the incubator and to avoid bubble formation.

Preferably, per an embodiment, the flow cytometer arrangement comprises a cleaning fluid supply apparatus connected to the first pump and/or the second pump, in order to supply cleaning fluid, especially ultrapure water, to the respective pump. Rather than ultrapure water, it is also possible, for example, to use a specific cleaning fluid, for example comprising chlorine, ozone or another oxidizing substance. This can achieve cleaning of pumps or other components, though it will be apparent that the particular cleaning fluid can, for example, also be released into further components by the pumps, for example the mixer, the incubator or the flow measurement cell.

Preferably, per an embodiment, the flow cytometer arrangement has a disposal tank connected to the first pump and/or second pump for supply of fluid from the pumps.

In this way, fluid which is no longer required can be reliably disposed of, this comprising, for example, sample fluid which is no longer required, dye which is no longer required, mixture which is no longer required, or else used cleaning fluid.

The disposal tank may be designed, for example, as part of the flow cytometer arrangement, though it will be apparent that, for example, it is also possible to use a direct connection to an outlet, for example a wastewater supply, for disposal. In this case, an activated carbon filter to eliminate the dye is connected in between.

In an embodiment, the flow measurement cell has a sample cannula for release of the sample fluid, mounted in a holder. The holder may be mounted, for example, by means of two O-rings. It may also be positionable by means of a thread.

It will be apparent that the flow measurement cell described herein may be regarded as an independent aspect of the disclosure.

Mounting in the holder has been found to be advantageous, per an embodiment, in order to enable use in different and non-constant environmental conditions. For example, stability to variations in temperature or vibrations is increased. The thread enables simple positioning of the sample cannula, such that the sample jet can reliably be adjusted, even during the measurement. For this purpose, the holder can be rotated in its environment, for example, by means of which it is also possible to adjust the position using the thread. By means of the O-rings, it is possible to establish a reliable seal, though it will be apparent that a different number of O-rings may also be used.

The components of the flow cytometer arrangement, per an embodiment, especially of the flow measurement cell, are in nonmetallic form and/or made of plastic, glass or ceramic. This has been found to be advantageous since the metallic constituents that come into contact with sample fluid can impair functionality owing to lack of biocompatibility.

Preferably, per an embodiment, the flow cytometer arrangement comprises a control device configured to control the pumps. This can achieve automated operation of the pumps. For example, such a control device may be executed as a standard computer, as a microcontroller, microprocessor, memory-programmable controller (MPC), application-specific integrated circuit (ASIC) or other programmable or hard-wired device. More particularly, it may contain processors and a memory, with program code stored in the memory, on execution of which the processors behave in a defined manner.

It will be apparent that the control device may also assume other functions than the control of the pumps, for example monitoring parameters or control of valves or other components.

The control device is preferably, per an embodiment, configured to control the first pump and the second pump in such a way that they pump simultaneously defined volumes of sample fluid and dye into the mixer. This can achieve defined filling of the mixer, such that accurately defined mixing ratios can be established.

The control device may be configured to control the first pump and the second pump in such a way that the second pump sucks in mixture from the mixer or incubator and, by synchronous operation of the first pump and the second pump, an operating pressure in the mixer and/or incubator can be kept at a defined pressure. As already described further up, it is thus possible to avoid damage to the mixer and/or the incubator and bubble formation since variations in pressure are prevented.

It will be apparent that, in the maintaining of defined pressures, it is the case that certain tolerances are technically unavoidable.

Preferably, per an embodiment, the control device is configured to control the second pump in such a way that the second pump sucks in mixture from the mixer or incubator. As a result, it is possible for a mixture to reach the second pump, especially in order subsequently to be used as sample jet.

Preferably, per an embodiment, the control device is configured first to trigger the pumping of sample fluid and dye into the mixer, then to wait for a predetermined incubation time, and then to trigger the suction of the mixture. The suction can be effected by means of the second pump. Waiting for the incubation time enables or improves binding of dyes to particles to be detected.

Preferably, per an embodiment, the control device is configured to control the first pump in such a way that it pumps sheath fluid into the flow measurement cell, and simultaneously to control the second pump such that it pumps mixture sucked in from the mixer or incubator into the flow measurement cell. This can achieve customary operation of a flow measurement cell with sample jet and sheath jet with just two pumps.

Preferably, per an embodiment, the flow cytometer arrangement also comprises an evaluation device configured to evaluate measurement results obtained by means of the flow cytometer arrangement. This can achieve automated evaluation of the measurement results, which, for example, enables further automation of the monitoring of a drinking water supply.

With regard to the configuration of the evaluation device, the details given further up for the control device are correspondingly applicable. It will be apparent that control device and evaluation device may also be executed as one unit or one component.

The evaluation device may be configured to generate two-dimensional plots. On a first axis of such a plot is plotted a first channel, and on a second axis is plotted a second channel. In the plot, a number of measured values are plotted at respective points. This can mean, for example, that each channel is assigned to a detector and the intensity thus defines the two-dimensional plot. For each combination of the two intensities, the number of such intensity combinations measured in each case is plotted in a particular time window. This results in characteristic patterns that give information as to the drinking water quality. More particularly, it is possible to find particular undesirable types of cells, such as particular bacteria, in particular regions of such plots, such that identification is readily possible. It is thus possible to react very quickly to certain events.

The evaluation device may be configured, per an embodiment, to define regions in the plots, in which case a predefined action is triggered on exceedance of a number of measured values within a region. Such a predefined action may, for example, be an alarm. It may also be another kind of action, for example the switching-off of the drinking water supply or the switching-on of particular disinfection measures.

It will be apparent that the flow cytometer arrangement of the disclosure provides, per an embodiment, a system that enables automated, reliable and continuous, and also rapid, monitoring of drinking water quality. A measurement as can be made by the flow cytometer arrangement described herein can be performed, for example, in the order of magnitude of 15 minutes to 25 minutes, especially 20 minutes. This enables virtually instantaneous recognition of events that adversely affect drinking water quality, and hence enables an immediate reaction and triggering of suitable countermeasures. The security of the drinking water supply is thus distinctly increased.

It will further be apparent that, by means of flow cytometry, as described herein per an embodiment, all or at least virtually all cells present in the sample fluid can be detected. This constitutes an advantage over the known AMK method. The significant reduction in the measurement time from about 72 hours to a few minutes means that precise, realistic results concerning the microbial flora in the water are available online to the user. To date, this has been possible only for chemical and physical parameters.

Flow cytometry can be used in order to determine the total cell count (TCC), high nucleic acid (HNA), low nucleic acid (LNA) and living/dead cells in water samples. It is also possible to recognize specific cells by means of specifically docking dyes.

The flow cytometer arrangement of the disclosure is usable at the site of sampling, i.e. outside the laboratory, and is ready for use round the clock. Furthermore, robust and precise flow cytometry detection is thus possible. Automated sample preparation, such as sampling, staining and incubating, may be provided, automated evaluation of the measurement results may be provided, an alarm in the case of events may be provided, data archiving, for example in a database, may be provided, interfaces for process control may be provided, and monitoring of the fluids, for example cleaning solution, ultrapure water, sheath fluid or dye, may be provided. The flow cytometer arrangement of the disclosure is typically designed for constant operation, i.e., for example, 24 hours per day and 7 days per week, and it may be immune to variations in temperature and conditions in industrial environments. In addition, remote access may be provided, for example via ethernet or other network technologies.

A reliable measurement system is provided for on-site use, which detects and provides the general and hygienic microbial condition of the water and bacterial activity within short time intervals.

More particularly, per an embodiment, the flow cytometer arrangement described may be suitable for use outside laboratories, for example in water extraction, water treatment, water distribution or in industrial plants, and may therefore be immune to physical circumstances that exist at these sites, such as temperature, variations in temperature, varying air humidity, dust, particles and vibrations. It is possible by means of flow cytometry to precisely detect particles and bacteria even outside laboratories.

Flow cytometry is based in principle on the staining of living and dead cells by means of DNA dyes that bind to intact or damaged DNA.

With the aid of SYBR Green-specific green fluorescence, it is possible to distinguish microbiological, intact cells from DNA-free, inorganic particles. For example, propidium iodide (PI) can penetrate the perforated or damaged cell membrane of dead cells, but not the intact membrane of living cells. This property can be employed in flow cytometry, for example in the arrangement described herein, for distinction of living/dead cells.

After staining and incubation, the microorganisms and particles are typically flushed individually through a glass capillary and illuminated with a focused laser beam in order to excite the DNA dye. If the laser hits a cell or a particle, the scattered light is detected in the scattered light channel and the light emitted by the cells is detected via the fluorescence channels. The flow cytometer arrangement of the disclosure can also achieve the effect that all process steps for a completely automated online operation can be integrated into a compact measurement device suitable for industry. "Completely automated" shall be understood in connection with the present description to mean that the device works faultlessly without human intervention over a period of at least two weeks. In addition, another problem to be solved is that the individual process steps are to be designed for failsafe operation and, for this purpose, possible disruptive influences that could lead to failure must be absorbed or compensated for.

The flow cytometer arrangement may contain, for example, in a compact housing, one or more syringe pumps or syringe pump units, at least one laser module, means of data acquisition (DAQ), a motor control board, a novel compact optical detection unit, at least one mixing unit for sample processing and preparation, at least one incubator, an instrument controller, at least one temperature controller for the measurement reaction and/or samples, application interfaces for performance and control of the measurement routines, control of the apparatus components, detection and evaluation of the sample parameters, transmission of the measurement results and data, and if necessary the issue of the alarm message. It will be apparent that any sub-combination of the components just mentioned may also be present. In order to enable non-laboratory use outside standardized environmental conditions, all components may be accommodated in a compact instrument housing suitable for industry, in which case the individual components are likewise of compact and space-optimized size. By means of suitable supply/removal of air and/or heat and component cooling or component heating, the conditions within the housing are adjusted in order to provide maximum uniformity in the measurement environment independent of the conditions at the setup site of the device.

The disclosure also provides, for example, a method of measuring microbiological and/or physical sample parameters and/or of subsequent data evaluation.

Every water varies in its microbiological structure. After the detection of the individual events by means of flow cytometry detection, the signals of two measurement channels can be represented by their signal strength and, according to the combination of the measurement channels, corresponding fluorescence and scattered light plots can be created. It may be the case here that these plots are evaluated by means of gates (regions) that are defined in the plots. Gates are to be correspondingly defined in the respective plots and their limits fixed.

The method of the disclosure may envisage the following, for example, for evaluation via gates:
- detection/representation of the number of events in all defined gates,
- distinction of LNA and HNA bacteria,
- distinction of active and damaged cells.

By fixing the values of individual regions in the gates and the combination of different gates in individual plots or over multiple plots, it is possible in a further embodiment to define warning and alarm conditions, in which case, when individual predefined conditions are attained in the water or fluid to be analyzed, a warning or alarm is automatically triggered.

Such events (for example warnings and/or alarms) may be issued and transmitted as follows:
- sending of a measurement protocol via email,
- acoustic/optical alarm (for example lamp on the device),
- issuing of analog and digital signals (for example to an MPC),
- via ethernet and/or the customer's control system.

Event definitions may be adapted, for example, to the respective plot or to the water to be analyzed, since every water has different cloud patterns or fingerprints. Such cloud patterns or fingerprints may especially be representations of the plots mentioned.

According to one measurement principle, differential measurements between two or more measurements can be used to express the respective measurement data relative to one another. For example, measurements on identical water samples over time, for example every 30 minutes, under constant conditions give only minor changes. If, for example, an event occurs—for instance the infiltration of rainwater, contamination with liquid manure or a functional fault in the treatment process—the subsequent fluorescence and scattered light plots will change within a short time. It is thus possible to react immediately to microbiological changes.

Warning and alarm criteria can be configured and issued as required.

A method can enable, individually or in combination, the detection and/or evaluation of the total number of all events (detected particles and/or cells), total number of cells (active and damaged), or total detection of all particles (particle measurement channel).

By definition of gates, in an embodiment, the number of events (detected particles and/or cells) in all defined gates can enable distinction of active and damaged cells and distinction of LNA and HNA bacteria.

Measurement results are, per an embodiment, preferably represented as a graph in the form of a 2D plot, i.e. the plots are preferably 2D plots. However, they may also be 3D plots, histogram plots, history plots and/or density plots.

It is possible to issue data as a PDF measurement protocol, CSV measurement protocol via ethernet and/or via remote access.

It is also possible to make a distinction between intact and damaged cells. This may be advisable, for example, in order to conduct a verification of disinfection measures, for example by means of ozonization or chlorination. For this purpose, a detection of living cells may be conducted. Oxidants cause severe damage to the cell walls in the case of bacteria. With propidium iodide, it is possible to selectively stain only the membrane-damaged cells and hence distinguish them from intact bacteria. Flow cytometry detection, combined with staining methods, also enables statements about the activity or viability of microorganisms in drinking water. The flow cytometer arrangement described herein permits analysis and understanding of the kinetics of the disinfections. More particularly, water supplies are thus provided with a compact and robust apparatus and a corresponding method by means of which disinfection measures can be evaluated and verified directly on site. It will be apparent that this may also constitute an independent aspect of the disclosure.

The disclosure also relates to a method and an apparatus for synchronous operation of two or more electrically coupled and motor-driven injection units. These may be used within the flow cytometer arrangement described herein, but may also be regarded as an independent disclosure.

In the case of such an injection unit, synchronous operation of at least two electrically coupled, motor-driven injection units may be provided in order—especially in the flow cytometer arrangement described here—inter alia to precisely mix fluids, for example in a specific mixing and reacting unit especially provided optionally in the flow cytometer arrangement described herein, and to focus and transport them. The use of the injection unit of the disclosure here is not limited to flow cytometers.

Known injection units are used for various purposes, for example in order to eject fluid continuously over time, for example for dosage. It is possible here, for example by means of a control application, to parametrize the injection unit and start the process. Relevant parameters here may, for example, be a volume to be drawn up or ejected, and a speed (volume per unit time) at which this is to be accomplished. In addition, an injection unit may be equipped with an additional motor-driven rotation valve in order to draw up fluids from different sources, or in order to enable release to different target conduits. In order to avoid jerky movements at the start or end, it is customary to use what are called ramps, corresponding, for example, to an acceleration on startup until the desired maximum speed has been attained.

With the execution described herein, as well as individual operation of such an injection unit, it is possible to synchronously operate two or more pumps or injection units. The advantages, per an embodiment, of such parallel synchronous operation are firstly the option of very precisely mixing two or more fluids in a given ratio. It is possible with preference here to use mixing components (for example butterfly mixers) that require constant speeds of the fluids to be mixed, in order to assure high mixing. A further advantage of synchronous operation, per an embodiment, is the option of transporting fluids from one injection unit to another. It is found here to be advantageous when a (starting) injection unit forces the fluid to be transported, while the (target) injection unit draws it in. The precision of synchronization here is of crucial significance since variances can give rise to high pressures. In addition, synchronous expulsion of two fluids can achieve hydrodynamic effects as required, for example, in flow cytometry.

The disclosure also relates to a detection unit which can be used in the flow cytometer arrangement described herein, but which can also be regarded as an independent disclosure.

The detection unit may also comprise or take the form of an optics monoblock. More particularly, it may be the case that some or all modules and components needed for flow cytometry detection, especially flow cell, optical filters, detectors, transimpedance amplifiers, signal detection and processing, laser and light in-coupling optics, are combined in a novel, symmetric arrangement to form a detection unit that has preferably been worked, especially milled, from a solid material, preferably per an embodiment in the form of a monoblock. In this way, the detection unit becomes not only compact and largely dust-tight, but also highly mechanically stable.

Detection units and components thereof may be in a fixed arrangement in a housing that has been manufactured in one-part or one-piece form from a solid material. It is also possible to use detection units having a housing consisting of two or more parts. More particularly, it may be the case that all constituents of the detection unit are accommodated in the housing. However, the execution of the disclosure is not limited thereto, but also comprises further execution variants in which individual components are arranged or provided outside the monoblock or housing.

In the solid material, in an embodiment, the mechanical removals of material in the main body can be implemented only where necessary, in order that the mechanical stiffness remains as high as possible. The higher the mechanical stability, per an embodiment, the more precisely the device can work.

A monoblock construction and the higher stability and compactness gained thereby also permit local applications in industrial environments. The greater immunity to the physical circumstances of temperature, air humidity, dust and vibrations meets the elevated demands of the individual industrial scenarios.

In one embodiment, a symmetric design of two opposite lenses for each of two optical measurement channels is implemented. All that this requires is, for example, another one beam divider and two color filters in each case.

Reduction in the beam dividers and mirrors can enhance optical efficiency.

The optics monoblock may contain all the components and modules needed for flow cytometry detection, for example light source, laser module, flow measurement cell, light in-coupling, beam divider, filter, optical detectors with transimpedance amplifiers, data acquisition and processing (DAQ). An FCM device is preferably intrinsically complete.

The disclosure also relates to a double-slit stray light stop. This may be used in the flow cytometer arrangement described herein. However, it is not limited thereto; it may instead also be regarded as an independent aspect of the disclosure.

In flow cytometry, apart from the fluorescence color measurement channels, the light scattered forward and to the side is typically also of interest. The light scattered forward gives information about the size of bacteria and particles, and that to the side information about their structure and shape.

Nowadays, in flow cytometry arrangements, hole-slit or inverse stops are typically positioned in front of the optical detectors, which may be positioned either horizontally or vertically, in order to shade the direct light scattered forward or the indirect light scattered to the side.

This type of light suppression always means a compromise between excessively high signal offset and excessively high suppression of the useful signal. The function of the double-slit stray light stop of the disclosure is, for example, to provide optimal signal offset suppression without impairing the useful signal. Preference is given to integration of the stop in combination with an optical filter in existing detection units, preferably an optics monoblock of the disclosure.

This can be achieved in that it enables an apparatus in flow cytometry to allow the light scattered to the side and forward to hit the detector in such a way that a static signal offset is suppressed and the scattered light, caused by particles and bacteria, hits the detector without impairment of signal quality.

The double-slit stop of the disclosure can be adjusted exactly to the height of the light beam by means of an integrated vertical guide in order to obtain a useful optical signal and rule out distortions by scattered light.

Advantageously, per an embodiment, with the double-slit stray light stop, virtually the entire bandwidth of the optical measurement signals is usable, since light reflected directly into the optical detectors is avoided.

A detection unit or detector arrangement as described herein also comprises, per an embodiment, as light source, a laser with integrated fiber coupling. However, use is not limited to the detection unit or detector arrangement as described herein, but can also be regarded as an independent aspect of the disclosure.

In order to distinguish cells having a DNA or RNA core from particles, in flow cytometry, the cells stained with fluorescent dye are typically excited by laser light with tightly defined wavelengths. This monochromatic light frequency or the wavelength must be exceptionally stable in order to avoid measurement errors in the signal detection.

The light source is coupled into fibers by means of adjusting units completely offset from the laser or internally decoupled in the laser module, which usually enable lateral positioning (x and y direction) and positioning in z direction and tilting. A disadvantage of arrangement of the laser light source in an optical fiber (usually single-mode fiber) is that this mode of coupling is sensitive to shaking, vibrations and temperature fluctuations. However, their use in laboratory flow cytometers usually works impeccably in the laboratory environment due to well-standardized conditions.

Since flow cytometry detection is to be implemented outside the laboratory and especially under non-standardized conditions, but with a measurement accuracy corresponding to laboratory flow cytometers, a laser system that fulfills these demands is to be provided. A further criterion is the extension of the lifetime of the laser light source in 24/7 operation. A disadvantage of standard solid-state lasers is that their lifetime in the case of 24/7 operation or in the case of constant continuous operation is limited to about one year. In order to ensure sustained use for several years, preference is given to using a semiconductor laser (diode).

Since such diode lasers provide the application-based light beam quality only in combination with a matched single-mode fiber, the solution provided is a fiber-coupled diode module.

This fiber-coupled diode module can also be referred to as a diode laser module with integrated fiber coupling. A laser diode support is designed, per an embodiment, such that it includes not just laser diode and collimation lens but also a focusing lens and the fiber positioning. The fiber coupling unit integrated into the laser diode support includes the lateral positioning (x, y direction), the focusing and an angle adjustment in both axes.

Fine adjustment screws accessible from the reverse side of the module or device are preferably responsible for the angle adjustment and focusing. The fine adjustment screws mounted to the top and side serve for lateral positioning.

On completion of positioning of the optical fiber in the detection unit, by means of fixing screws likewise accessible from the reverse side, the lateral adjustment unit is screwed to the laser diode support.

By combining all functions, especially laser diode, collimation and focusing lens, and fiber coupling unit in one body, it is possible per an embodiment to absorb disruptive influences such as vibration or mechanical movements resulting from thermal influences. Sufficient long-term stability, especially for flow cytometry applications, can thus be achieved.

A further advantage, per an embodiment, is higher compactness of the arrangement, higher mechanical stability, and substantial insensitivity to fluctuations in temperature and vibrations.

The detection unit or detector arrangement described herein, per an embodiment, also comprises a flow measurement cell unit. However, the use is not limited to a detection unit or detector arrangement as described herein, but may also be regarded as an independent aspect of the disclosure.

A flow measurement cell or flow measurement cuvette is a central fluid optics component of a flow cytometry arrangement.

The flow measurement cell typically includes the supply of the sample stream and sheath stream fluid, a quartz glass cuvette, and the mechanical consolidation of these components and functions.

The flow measurement cell ensures that the cells of a sample fluid are flushed through singly and always in the center (in the optical focus). This is accomplished by means of what is called hydrodynamic focusing. The geometric dimensions and ratios of the sample stream and sheath stream feeds influence the sample jet diameter, the sheath stream volume and the stability of the sample jet. The sample fluid is injected into a faster-flowing carrier fluid and guided through a constriction in the feed channel within the flow chamber. This constriction increases the flow rates proportionally to the change in cross section of the channel. Thus, the cross-sectional ratio between sample fluid and carrier fluid also varies depending on the relative flow rate.

The flow rates are adjusted such that the reduction in the sample cross section forces the cells to line up within the fluid. In addition, the change in speed also increases the distance between the individual cells.

The great advantage of hydrodynamic focusing, per an embodiment, is that the flow rates can be adjusted very efficiently and the sample fluid can be guided very stably.

More particularly, the flow measurement cell in flow cytometry arrangements or flow cytometer arrangements can be used for precise detection of individual cells and particles in aqueous solutions.

It may be advantageous here to obtain a stable, pulsation-free sample jet in the flow cuvette in the center of the measurement channel. For this purpose, as well as a very precise, volume flow rate-regulated fluid supply, the vertical position of the sample supply cannula is crucial.

It should be possible to undertake optimal positioning of the sample cannula not just in the assembly of the unit; it should also be adjustable during operation. Such a flow measurement cell unit is to give the appropriate measurement results in a precise and stable manner even outside laboratories. Therefore, the measurement cell design is chosen, per an embodiment, such that the varying coefficient of expansion of the different materials, especially quartz glass, aluminum and plastic, do not have any adverse effects on the lateral position of the cuvette channel.

This can be achieved in that the sample feed is vertically positioned during a calibration measurement by providing a needle for application of a sample with a laterally positioned, guided sample needle holder made from two O-rings. Apart from the positioning and guiding of the needle holder, the two O-rings mounted at the ends serve as a mechanical brake in order to prevent, after complete adjustment, independent loss of adjustment caused by vibrations, for example.

The sample needle holder may be provided with a fine winding on the outside. The slope thereof is correlated with an achievable vertical positioning resolution. In one embodiment, the fine winding may, for example, have a slope of 0.25 mm in order to achieve vertical positioning resolution of preferably less than 1 μm.

Preferably, per an embodiment, the flow measurement cell unit comprises or has been manufactured from the materials PEEK, aluminum and quartz glass. The materials may especially have a non-correlating thermal coefficient. In order to compensate for this, the rest for the measurement cuvette is spring-mounted, especially by means of cup springs. In order to assure the lateral stability of the rest, there is at least one O-ring mounted on its circumference. It is also possible, for example, to mount two O-rings. What can be achieved in this way is that the variance in length of the different materials over a temperature range from especially about 60° C. to 70° C. is compensated for.

The sheath stream fluid which is introduced at one point into the circular distribution ring via a channel is preferably intended to form a homogeneous flow around sample cannula and sample jet. Therefore, the fluid is straightened by means of a perforated plate.

The disclosure also encompasses a method performable, for example, by means of the flow cytometer arrangement of the disclosure for evaluation of flow cytometry scatter channel measurement data, which preferably serves to determine the turbidity of fluids. This method has an independent inventive significance and is not limited to the use of the flow cytometer arrangement described herein.

The measurement data obtained in the flow cytometry are additionally used for the determination of turbidity.

Flow cytometry (FC) will increasingly succeed obsolete methods in the sector of water quality determination among others. This test method, known primarily from medicine, has thus generally become established for analysis of fluids. As well as the properties measurable by flow cytometry, such as number and activity of bacteria, general turbidity is also of interest. This turbidity value is traditionally measured with a device intended specially for that purpose. A disadvantage has been found to be that, even when known measurement devices based on flow cytometry are used, it has been necessary to date to measure turbidity separately since a conventional flow cytometer cannot determine turbidity. Directly compared to a flow cytometer, turbidity measurement devices are substantially more simple and thus also more economical. But if a flow cytometer arrangement or a flow cytometer is in use in any case, it is also possible by the method of the disclosure to use the flow cytometry measurement data to conclude the turbidity of the fluid being analyzed. It is possible here to use measurement data in raw form, i.e. before any corrections by signal processing. It is possible, in the case of specific implementations, to use synergistic effects of signal processing. What has been described here is the actual method. The use of synergistic effects is application-specific.

Historically, turbidity has been elicited especially by a manual transmission test. This was done using the recognizability of numbers behind a particular amount of the fluid to be assessed as indicator. This method was replaced by standardized turbidity units (for example FAU, FNU, FTU, NTU, TE/E and EBC). The sole fluid for which these standards show equivalent results is the fluid formazin. In the case of real samples, deviations, in some cases large deviations, between the different standards are to be expected. The measurements ascertained by the method presented here, owing to the properties of the measurement system used, do not correspond to any of the standards mentioned. Owing to the wavelength of the light source of 488 nm which is frequently used in flow cytometry (for example in the case of a laser) compared to the wavelength fixed in specification ISO 7027, the method described herein cannot directly cover the entire spectrum of fluids. With suitable weighting parameters, however, it is possible to approximate the results to the desired measurement standard.

The method of the disclosure, according to the availability of the channels of the flow cytometer or of the flow cytometer arrangement, should be employed either with forward scatter or side scatter. It is also possible to evaluate both channels in order to extend the range in which the value ascertained corresponds to a standard.

The "Adaptive implementation" section describes how the weighting parameters can be adjusted on the basis of the input parameters in order to increase the range of values equivalent to a standard method. This may in turn correspond to a specific implementation of the basic method.

Control and/or evaluation software includes, per an embodiment, algorithms that permit calculation of the corresponding parameters as an option.

A further method described herein, which can be used, for example, with the flow cytometer arrangement described herein, but may also constitute an independent aspect of the disclosure, provides the option of recognizing cells in the state of cell division on evaluation of flow cytometry measurement data. This method is described in association with the above-described flow cytometer arrangement, but does indeed have independent inventive significance. Application of the method to measurement data discovered in other flow cytometry applications is likewise encompassed by the disclosure.

Flow cytometry is widespread and even well-established for decades in the medical sector for purposes including blood analyses. What are usually examined are particles of 2 μm or larger in size in fluids. Newer sensors and finer and faster signal scanners in modern flow cytometers are achieving measurement accuracy that permits coverage of significantly smaller bacteria in some cases. This is increasingly being utilized in water quality measurement by recording bacterial cultures living in water. Such a measurement represents a fixed state at the measured time point. Without further information, it is not possible to make any conclusion as to the past or future state of the water.

Bacteria propagate asexually in accordance with the principle of cell division, for example by binary fission or pullulation. The rate of division depends, in particular, on environmental factors such as temperature and nutrient supply or nutrient availability. The optimal temperature depends on the respective specific type of bacteria. Likewise bacterium-specific is a required type of nutrient. Since a flow cytometer is not capable to date of eliciting the type of a measured cell colony, it is thus also not possible to determine whether a specific temperature is beneficial or inhibiting. The detection of nutrients in a fluid is a complex process and hence well outside the abilities of known flow cytometers. Nevertheless, a sample such as water, for example, will have a certain probability of containing a certain number of bacteria that are currently at the division stage.

A flow cytometer or flow cytometer arrangement is thus to be provided, with which time and intensity in particular can be sufficiently finely resolved to recognize bacteria in the cell division phase by a method that can be considered as an independent aspect of the disclosure. For this purpose, the data are analyzed for maxima and minima. If two maxima occur in rapid succession and the minimum point in the middle attains a certain depth, there is a high chance that there will be two cell nuclei that come from a cell in the process of division. The recognizing of this specific feature has two benefits.

If, for better resolution of detail, the area of a pulse is integrated and used for particle identification, the result in the case of two successive signal pulses is a slight distortion. This area error can be corrected.

The number of particles at the cell division stage is compared to the generally recognized particles. This results in a bioactivity factor. This factor may be either over all particles or cluster-specific, and is ultimately a matter of evaluation. The finding of the bioactivity factor permits conclusions as to nutrients present, but also to oxygen.

The fluid to be analyzed may be shaped to a thin jet. This jet may be bombarded with an exciting light source, especially with a laser. The particles present in the fluid react in accordance with their optical properties to the light source and result in a measurable optical pattern.

For measurement of the signal generated by the particles, it is possible to use optoelectronic sensors, for example photodiodes or photomultipliers. This is true not just of the method described specifically here, but quite generally. The photodetectors generate an electrical signal that can be converted digitally. The transformation is effected so quickly that the distance between the cell nuclei can be assessed with maximum accuracy. The digital signal is continuously examined for local maximum values, for example peaks. At the same time, or no later than after recognition of a local maximum, the signal is examined for local minima.

If the separation between two local maxima goes below a certain limit, this is an indication that the pulses are not independent. For assessment as to whether the cell is truly at the division stage, further parameters may be cited. The parameters usable also depend on the accuracy of the measurement system. For improvement, the permissible difference between the two maxima can be limited. Since the cell nuclei are the same type, the measured size of the local maxima should be virtually identical. Although there are various conceivable scenarios in which identical cell nuclei result in different maxima (false negative), it can generally be assumed that the measured amplitude is within the same size range.

A further indication of dependence of two successive pulses is the height of the minimum value enclosed. This is expressed in relation to the surrounding maximum values. If the minus is too large, i.e. virtually equivalent to the enclosing maxima, this indicates too low a division and is thus an exclusion criterion.

It should be mentioned that cell division can typically be recognized only within a particular time window of cell division. This is taken into account in the determining of an activity index. Geometric factors or imaging errors should also be taken into account. All these sources of error that generally lead to a lower activity count can be compensated for with a factor to be determined for the measurement system. This results in an activity index subject to a probability distribution. This division may differ significantly from normal distribution. According to the end use, this distribution can also be neglected.

In this connection, it is pointed out that all features and properties described in relation to the apparatus, but also procedures, are also applicable mutatis mutandis with regard to the formulation of the method of the disclosure and are usable in the context of the disclosure and are considered to be included in the disclosure. The same also applies in the reverse direction, meaning that construction features mentioned only in relation to the method, i.e. apparatus features, can also be taken into account and claimed within the scope of the apparatus claims, and likewise form part of the disclosure.

BRIEF DESCRIPTION OF THE FIGURES

Further features and advantages will be inferred by the person skilled in the art from the working examples described hereinafter with reference to the appended drawing. The figures show:

FIGS. 4 to 7: a double-slit stray light stop,

FIGS. 12 to 15: a flow measurement cell,

DETAILED DESCRIPTION

Figure 1:
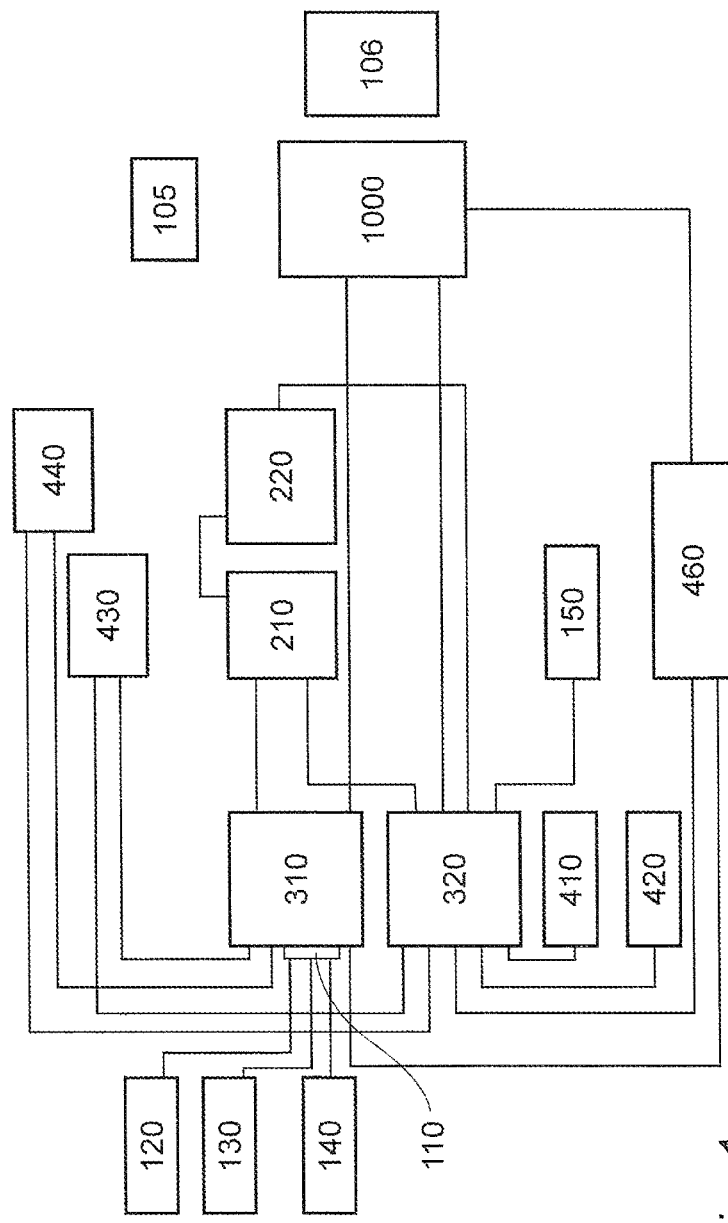
FIG. 1: a flow cytometer arrangement in one working example of the disclosure.

In the figures, identical or corresponding elements are each labeled with the same reference numerals and are therefore, if not appropriate, not described again. The disclosures present throughout the description are applicable mutatis mutandis to identical parts having identical reference numerals or identical component designations. The statements of position chosen in the description, for example at the top, bottom, sides etc., are also based on the figure directly described and shown, and in the event of a change in position are applicable mutatis mutandis to the new position. In addition, it is also possible for individual features or combinations of features from the different working examples shown and described to constitute independent or inventive solutions.

FIG. 1 shows a schematic of a flow cytometer arrangement 100 in one working example of the disclosure.

The flow cytometer arrangement 100 comprises a detector arrangement 1000 designed to analyze a sample fluid and especially to detect cells present therein. Assigned to this is an evaluation device 106.

The flow cytometer arrangement 100 comprises an inlet connection 110, which should be regarded here as an element by which sample fluid to be analyzed is taken in. Connected thereto are a first withdrawal unit 120 and a second withdrawal unit 130, each of which is designed as a crossflow filter. These are intended to withdraw sample fluid from a continuous stream of water, for example from a water supply. The exact design thereof is discussed in detail further down. Additionally disposed at the inlet connection 110 is an individual sample intake 140, by means of which, in individual cases, individual samples can be supplied to the inlet connection 110.

The flow cytometer arrangement 100 comprises a mixer 210 and an incubator 220 downstream thereof.

By means of the mixer 210, sample fluid can be mixed with dye. The resultant mixture is then released to the incubator 220, the incubator 220 being designed to ensure appropriate conditions for the dye to be incorporated into the cells present and especially to dock onto a DNA or RNA. For this purpose, the incubator 220 is designed to heat the mixture supplied by the mixer 210 to a temperature of 40° C. for a period of 5 minutes. However, it will be apparent that other combinations of time and temperature are also possible in principle here.

In order to supply the mixer 210 and the incubator 220 and to draw off mixture therefrom, the flow cytometer arrangement 100 comprises a first pump 310 and a second pump 320.

The first pump 310 is connected to the inlet connection 110 on the inlet side. On the outlet side, it is connected to the mixer 210. The first pump 310 can thus be used to supply sample fluid to the mixer 210.

The second pump 320 serves to supply dye. For this purpose, the flow cytometer arrangement 100 comprises a first dye reservoir 410 and a second dye reservoir 420, each of which is connected to the second pump 320. On the outlet side, the second pump 320 is connected to the mixer 210.

The second pump 320 also serves to suck in mixture from the incubator 220 and to supply this mixture to the detector arrangement 1000. For this purpose, the second pump 320 is connected to the incubator 220 on the inlet side. On the outlet side, the second pump 320 is also connected to the detector arrangement 1000 in order to produce a sample jet in a flow measurement cell, described further down, of the detector arrangement 1000. The connections of the second pump 320 to the mixer 210 and to the detector arrangement 1000 are switchable here in such a way that it is possible to choose whether the second pump 320 pumps into the mixer 210 or into the detector arrangement 1000. Equally, the connections to the incubator 220 and to the dye reservoirs 410, 420 are each switchable, such that it is possible to choose whether the second pump 320 sucks in from the first dye reservoir 410, from the second dye reservoir 420, or from the incubator 220.

The flow cytometer arrangement 100 additionally comprises a secondary inlet 150 which is switchably connected to the second pump 320 and permits the supply of individual samples to the second pump 320. It is thus possible in principle to circumvent the preparation of samples or of mixtures shown and described, and to directly route a fluid into the second pump 320, which is to be supplied directly to the detector arrangement 1000 for evaluation. The mixture can likewise be dispensed there.

The first pump 310 additionally serves to supply sheath fluid. For this purpose, the flow cytometer arrangement 100 comprises a sheath fluid reservoir 430 in which sheath fluid is stored. The first pump 310 is connected on the inlet side to the sheath fluid reservoir 430 and can thus suck in sheath fluid from the sheath fluid reservoir 430. The connections to the inlet connection 110 and to the sheath fluid reservoir 430 are each switchable, such that it is possible to choose whether the first pump 310 should suck in from the inlet connection 110 or from the sheath fluid reservoir 430. On the outlet side, the first pump 310 is also connected to the detector arrangement 1000 in order to produce a sheath jet in the flow measurement cell already mentioned (not shown in FIG. 1). The connections of the first pump 310 to the mixer 210 and to the detector arrangement 1000 are each in switchable form, such that it is possible to choose whether the first pump 310 is to pump to the mixer 210 or to the detector arrangement 1000.

The flow cytometer arrangement 100 also comprises a cleaning fluid supply device 440. This is switchably connected to the pumps 310, 320. The cleaning fluid supply device 440 is designed to supply ultrapure water. Alternatively or additionally, it may be designed, for example, to supply chlorinated water. Thus, the pumps 310, 320 and components attached thereto, if required, can be cleaned with ultrapure water and/or with chlorinated water in order to remove any bacteria or other soiling present.

The flow cytometer arrangement 100 also comprises a disposal tank 460 connected to the pumps 310, 320. It is also connected to the detector arrangement 1000. In the disposal tank 460, it is possible to store fluids that are no longer required, and especially also fluids that have been used for purging and cleaning. The disposal tank 460 can regularly be emptied in accordance with the regulations.

The flow cytometer arrangement 100 also comprises a control device 105, which is likewise shown here only in schematic form. The control device 105 is designed to control the pumps 310, 320, and also to switch the valves mentioned or otherwise present (not shown in FIG. 1). The control device 105 can thus control the operation of the entire flow cytometer arrangement 100.

There follows a description by way of example of a typical mode of operation of the flow cytometer arrangement 100.

First of all, the first pump 310 is opened on the inlet side and sample fluid is sucked in from the inlet connection 110. This sample fluid may come either from one of the withdrawal units 120, 130 or from the individual sample intake 140. Likewise by means of the second pump 320, a defined amount of dye is sucked in from the dye reservoirs 410, 420. This can be effected either simultaneously or at different times.

Subsequently, the two first and second pump 310, 320 are opened on the outlet side, specifically toward the mixer 210. The connections to the detector arrangement 1000 are closed here. Thus, sample fluid and dye are pumped into the mixer 210.

The two first and second pumps 310, 320 are then actuated in such a way that they simultaneously release sample fluid and dye into the mixer 210. This is effected synchronously, such that sample fluid and dye flow homogeneously into the mixer 210.

The mixer 210 is designed so as to ensure thorough mixing of the sample fluid supplied with the dye supplied. The resultant mixture is then released to the incubator 220. The latter heats the mixture to a temperature of 40° C. for a period of 5 minutes.

The mixture prepared in this way is then sucked in by the second pump 320. For this purpose, the second pump 320 is opened and correspondingly actuated on the inlet side toward the incubator 220.

During the suction of the mixture by the second pump 320, the first pump 310 is operated synchronously in such a way that there is a constant pressure in the combination of mixer 210 and incubator 220. This prevents damage.

The correspondingly processed mixture is now present in the second pump 320. In order to be able to evaluate this, sheath fluid is also required. This is sucked in by the first pump 310 from the sheath fluid reservoir 430.

For analysis, both the mixture and the sheath fluid are pumped simultaneously into the detector arrangement 1000. For this purpose, the second pump 320 and the first pump 310 are opened on the outlet side and actuated such that the mixture and the sheath fluid pass synchronously into the detector arrangement 1000. The mixture here forms a sample jet through the flow cuvette already mentioned, while the sheath fluid generates a sheath fluid jet through this sample cuvette. By means of this sheath fluid, it is then possible to hydrodynamically focus the sample jet. This is discussed in detail further down.

This operation may be followed, if required, by cleaning of the pumps 310, 320 or else other components by means of ultrapure water and/or chlorinated water. Any contaminated fluids obtained here or else other fluids that are no longer required may be disposed of in the disposal tank 460.

Figure 2:
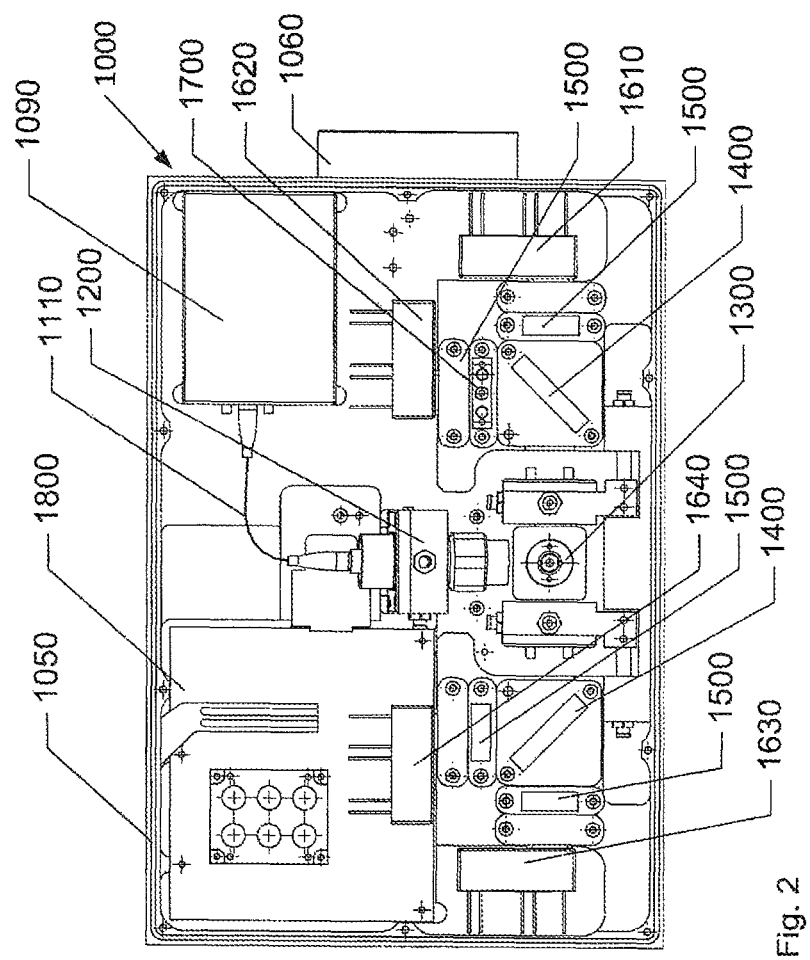
FIGS. 2 and 3: a detector arrangement.
Figure 3:
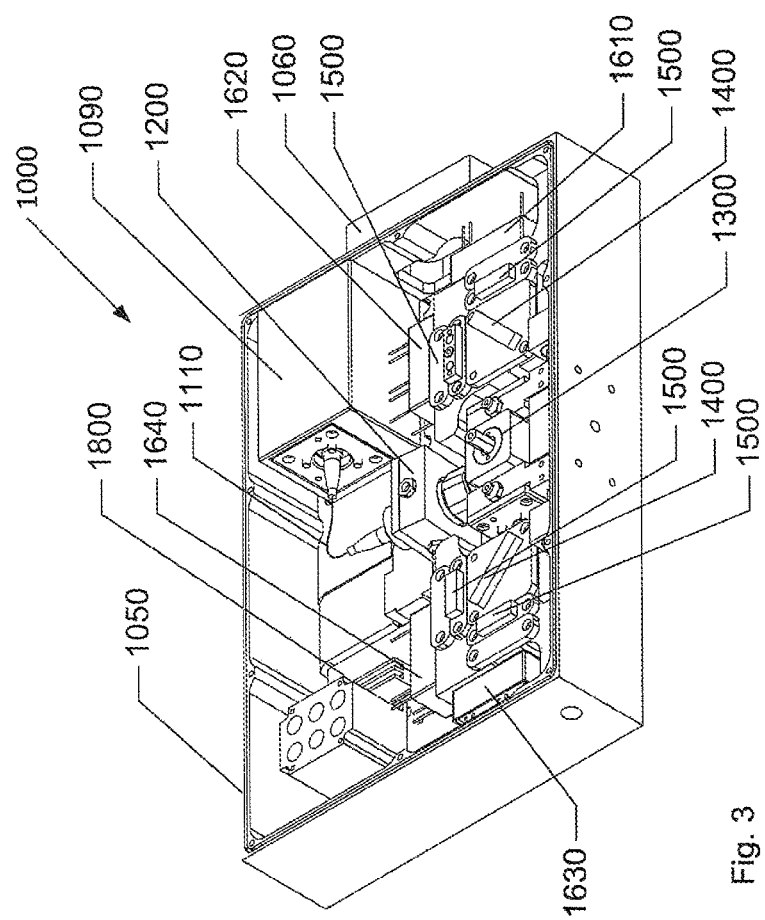
Figure 6:
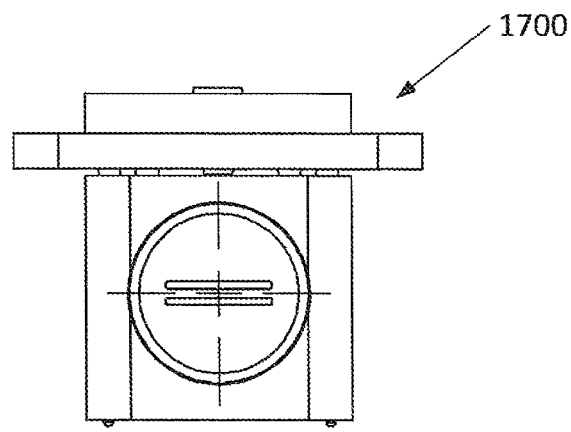
Figure 7:
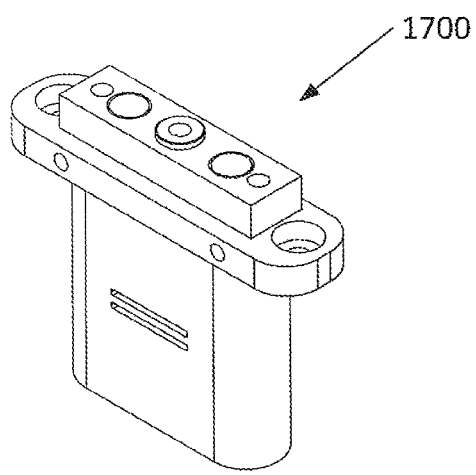
Figure 8:
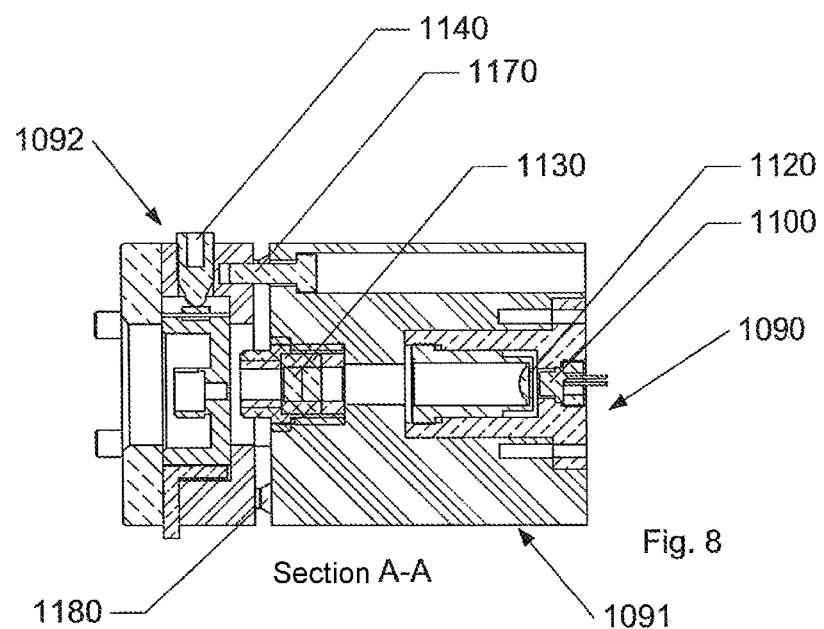
FIGS. 8 to 11: a laser unit.
Figure 9:
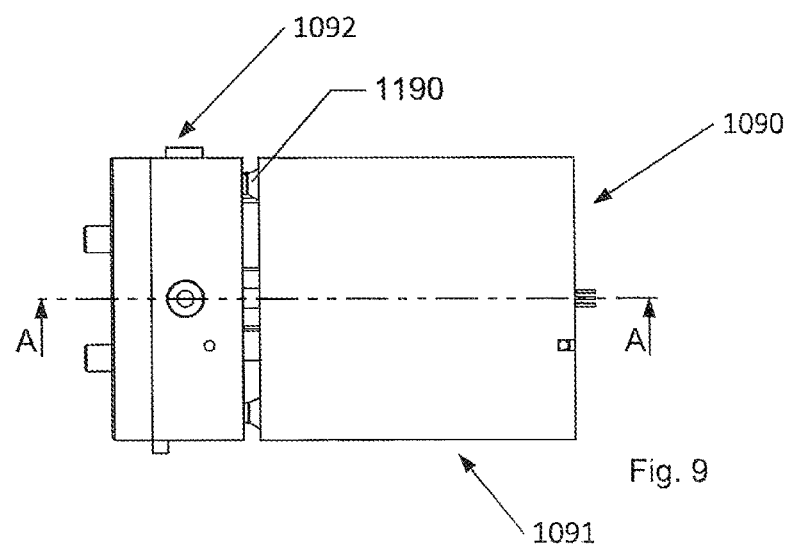
Figure 10:
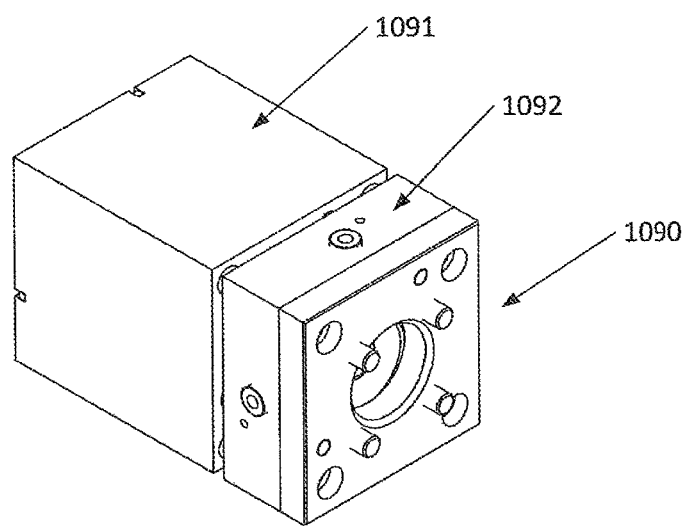
Figure 11:
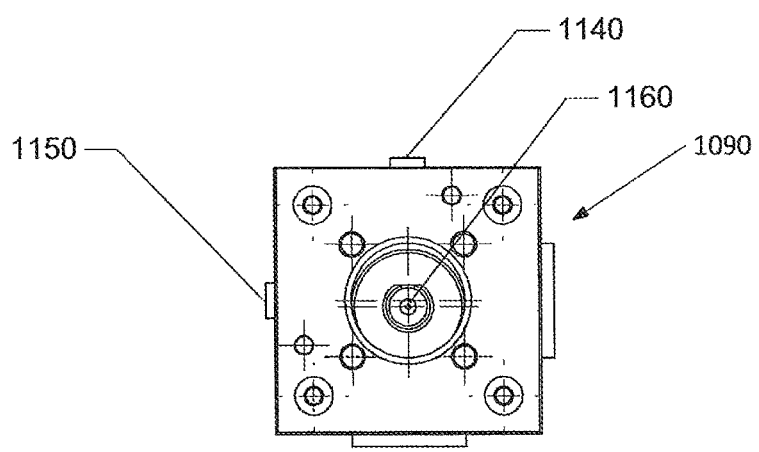

FIGS. 2 and 3 show the detector arrangement 1000 in greater detail.

The detector arrangement 1000 is present in a housing 1050 in the form of a monoblock or in one-piece form. The housing 1050 is formed here from a solid material, for example by milling. In the present case, it has electrical connections 1060 on its narrow sides.

In the housing 1050 there is a laser arrangement 1090 which is described in detail further down.

The detector arrangement 1000 comprises a flow measurement cell 1300 that will likewise be discussed in detail further down. Upstream of the latter are directing optics 1200 that will likewise be discussed in detail further down. Between the laser arrangement 1090 and the directing optics 1200 is provided an optical fiber 1110, by means of which a laser beam generated by the laser unit 1090 is directed toward the directing optics 1200. The directing optics 1200 guide and focus the laser beam in a defined manner onto the flow measurement cell 1300, through which the sample jet already mentioned with reference to FIG. 1 and the sheath fluid flow. The sheath fluid serves to focus the sample jet to a diameter of about 30 µm.

The bacteria present in the sample jet that have been labeled with the dye already mentioned further up scatter the laser beam laterally. The laser beam is likewise intrinsically scattered laterally at the flow measurement cell 1300. The scattered light is divided by two beam dividers 1400 arranged laterally relative to the flow measurement cell 1300 with regard to the laser beam. These beam dividers 1400 in the present case are non-wavelength-sensitive beam dividers.

The beam dividers 1400 divide the scattered light between a total of four detectors 1610, 1620, 1630, 1640. Bandpass filters 1500 are positioned upstream of each of three of these detectors, namely the detectors 1610, 1630 and 1640, and these filter out a respective small proportion of the optical spectrum, such that the respective detector 1610, 1630, 1640 detects only the corresponding portion of the optical spectrum. This enables wavelength-sensitive detection. It is also possible for the respective beam divider 1400 to take the form of a bandpass filter.

A double-slit stray light stop is positioned in front of one of the detectors, namely detector 1620, which will be discussed in detail further down. This suppresses the original laser beam which is intrinsically reflected at the flow measurement cell 1300. Positioned downstream of the double-slit stray light stop 1700 is a bandpass filter having an excitation wavelength of 488 nm. What this enables is the use of the wavelength of the laser beam, which is 488 nm in the present case, for detection by means of the detector 1620 as well.

In addition, the detector arrangement 1000 comprises evaluation electronics 1800 which ensure first processing of the data obtained by the detectors 1610, 1620, 1630, 1640.

Detectors 1610, 1620, 1630, 1640 have respective transimpedance amplifiers, which facilitates the evaluation of the signals obtained.

FIGS. 4 to 7 show the double-slit stray light stop 1700. This makes it possible for light scattered laterally and forward in flow cytometry to be allowed to hit a particular detector in such a way that a static signal offset is suppressed and the scattered light, caused by particles or bacteria, hits the respective detector without impairment of signal quality. In the present case, the detector is the detector 1620 already described.

The double-slit stray light stop 1700 can be adjusted exactly to the height of the light beam by means of an integrated vertical guide via guide pins 1730 that engage with compression spring pins 1720, or via a fixing and arresting screw 1740 and a fine adjustment screw 1710, in order to obtain an optimal useful signal and rule out distortions by scattered light. For this purpose, the reflected original laser beam can be directed onto a land 1750.

Advantageously, the double-slit stray light stop 1700 is usable virtually over the entire bandwidth of the optical measurement signals, since light reflected directly into the optical detectors is avoided.

FIGS. 8 to 11 show the laser unit 1090 in further detail and in different views.

The laser unit 1090 is divided into a laser section 1091 with integrated fiber coupling and a lateral fiber positioning unit or input coupling unit 1092.

The laser unit 1090 comprises a laser diode 1100 that generates a laser beam having a wavelength of 488 nm. Downstream thereof are a collimation lens 1120, a focusing lens 1130, and the already mentioned lateral fiber positioning unit or input coupling unit 1092. Adjustment is possible by means of a first fine adjustment screw 1140 in y direction and a second fine adjustment screw 1150 in x direction. The supply of the fiber 1110 already mentioned is achieved by means of a fiber connector 1160.

The input coupling unit 1092 is secured by means of two fixing screws 1170.

By means of a third fine adjustment screw 1180, tilting in x direction can be achieved. By means of a fourth fine adjustment screw 1190, tilting in y direction can be achieved.

FIGS. 12 to 15 show the flow measurement cell 1300 in greater detail. This especially includes a feed for sample fluid and sheath fluid. These are combined in a quartz glass cuvette.

The flow measurement cell 1300, which can also be referred to as flow cuvette, ensures that the cells of a sample fluid are flushed through individually and always in the center (at the optical focus). The geometric dimensions and ratios, especially of a sample stream and sheath stream feed, influence the sample jet diameter, the sheath stream flow rate and the stability of the sample jet.

The sample jet is supplied via a sample cannula 1320. It should be possible to adjust this sample cannula 1320 not just on assembly of the unit but also during operation.

A sample feed can be positioned vertically during a calibration measurement in that a needle for application of a sample is held with a laterally positioned, guided sample needle holder. The sample needle holder 1330 has an outer thread that engages with an opposing thread. In this way, simple adjustment can be undertaken in vertical direction by rotating the sample needle holder 1330. To the side of the sample needle holder 1330 are provided two O-rings 1360 that ensure sealing and fixing. These also act as a mechanical brake in order, after adjustment, to prevent loss of adjustment that can be caused by vibrations, for example. They also have a sealing effect.

The outer thread mentioned in the present case is a fine thread. This enables particularly exact adjustment.

The sheath fluid is introduced at one point into a circular distribution ring 1390 here via a sheath stream fluid channel 1304. The sheath fluid is intended to form a homogeneous flow around the sample cannula 1320 and the sample jet. For this purpose, in particular, a perforated plate 1380 is provided, by means of which the sheath fluid is straightened.

The flow measurement cell 1310 further comprises a rest 1340, a compression spring 1350 and two upper O-rings 1370 on the rest 1340 for fixing of the cuvette. The sheath jet is guided through the sheath stream fluid channel 1304. Sample and sheath fluid or further media are removed via an outlet 1308 after conclusion of the measurement.

The sample is fed from below through a sample feed 1306 provided beneath the unit. Assigned to this is a sheath stream fluid feed 1307.

The entire unit is enclosed in a mechanically stable manner and borne in a support 1302. This may be disposed in the housing 1050 already mentioned, which may especially be in the form of a monoblock, and may be removed as a unit with all constituents that have just been described, for example for exchange or for cleaning.

Figure 16:
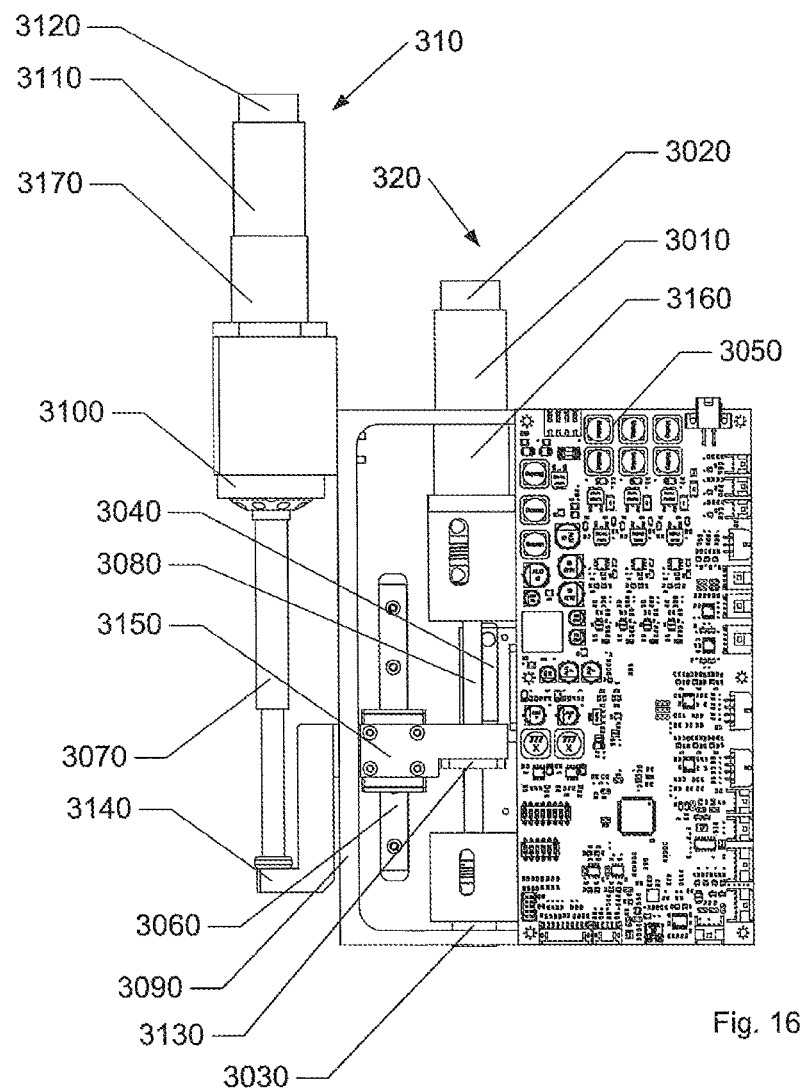
FIGS. 16 and 17: an injection unit.
Figure 17:
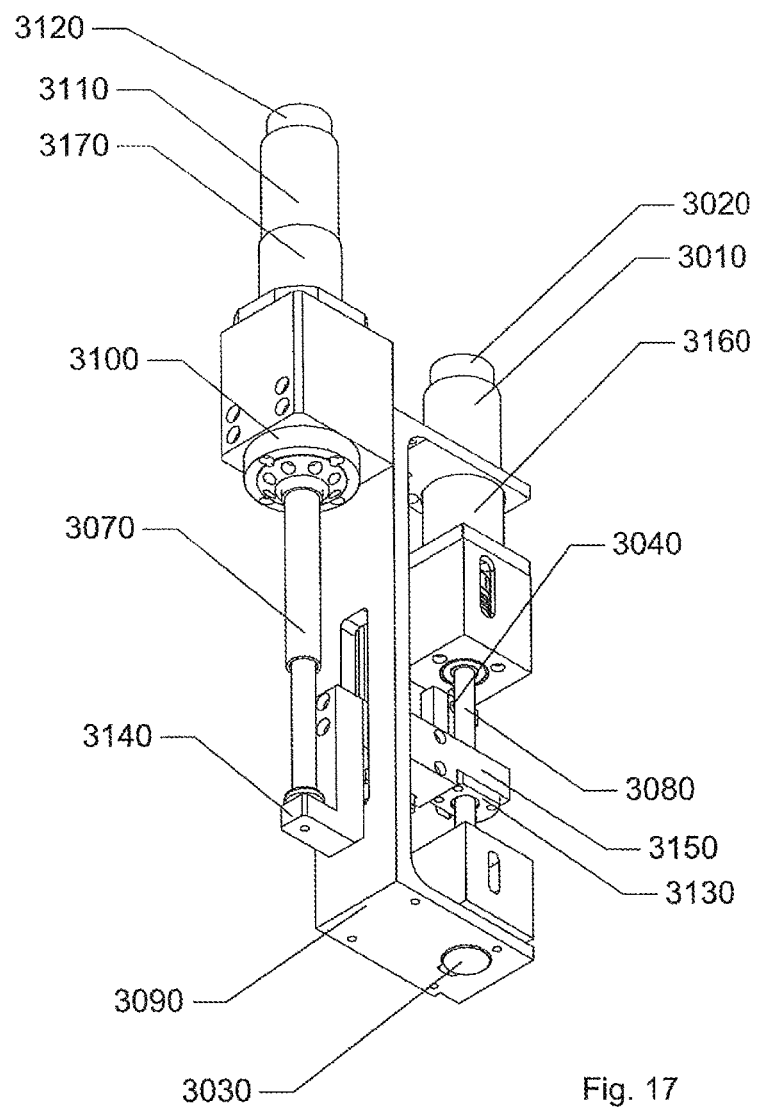

FIGS. 16 and 17 show an embodiment of an injection unit. This may be used, for example, for control of the pumps 310, 320 already mentioned with regard to FIG. 1. In the present case, it is shown correspondingly.

The pumps 310, 320 are driven by motors 3010, 3110. Assigned to these are respective motor encoders 3020, 3120, a position encoder 3030, and a reference sensor 3040. Assigned to the motors or injectors are respective individual independent motor controllers 3050, but these in the present context are connected to the software.

Each injection unit has a linear guide 3060 and an injector 3070 with assigned drive spindle 3080. For arrangement of the respective injection unit in a device, this has a syringe support 3090 that also bears the other elements.

Assigned to the injection unit for control of the media flow is a rotation valve 3100, which has its own motor 3110 and its own motor encoder 3120.

Assigned to an injection arm 3140 is a locking nut 3130 connected to a linear slide 3150. By means of a planetary drive 3160, it is possible to move the respective injector or, by means of a further planetary drive 3170, the rotation valve.

Figure 18:
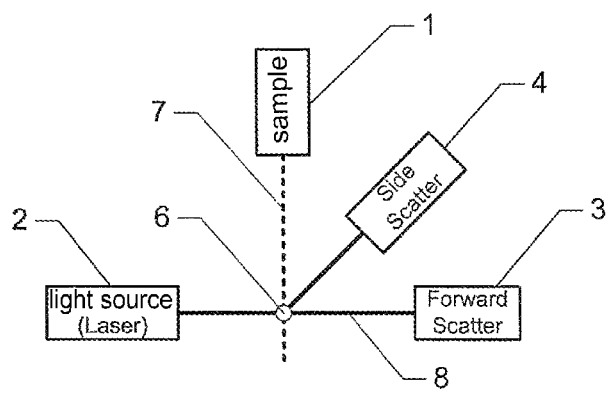
FIG. 18: a general principle of function.

FIG. 18 shows a schematic of a simplified diagram of the general principle of function of flow cytometry.

In principle, a sample 1 is shaped here to give a sample jet 7. This jet is irradiated by a light source 2. In the present case, this is a laser, for example. If the light beam hits a particle 6, the result is a shadow on a forward scattering sensor 3, while a scattered light 8 falls on a side scatter sensor 4 to the side.

Figure 19:
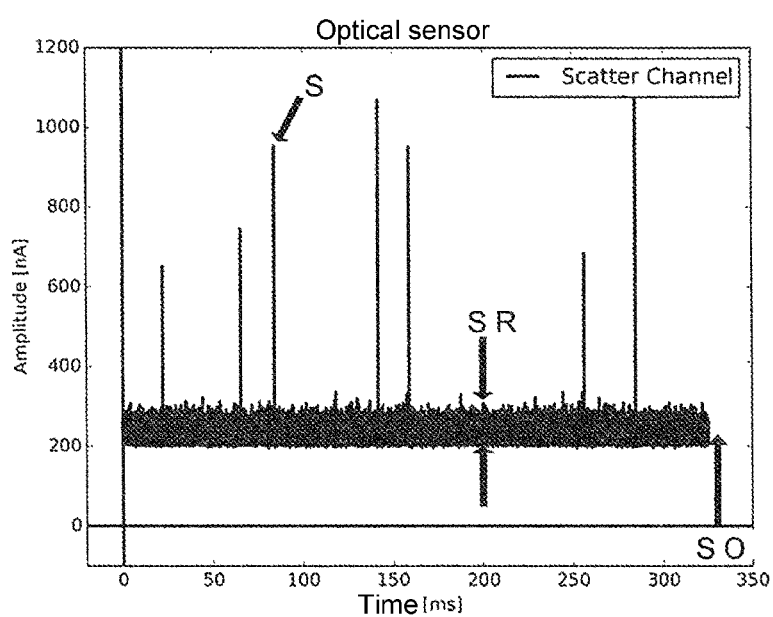
FIG. 19: unprocessed measurement data from a scatter channel of a flow cytometer.

FIG. 19 shows, by way of example, unprocessed measurement data from a scatter channel of a flow cytometer. These measurement data can be used to calculate parameters usable with appropriate weighting to calculate turbidity. The graph shows the electrical signal that has been converted digitally, in the present case as a current signal.

The exact type of signal is unimportant here, or is dependent on the sensor used. A standard output parameter from an optoelectronic sensor is an electrical current.

SO denotes a general signal offset. SR denotes signal noise. S denotes a signal caused by particles, i.e. the general useful signal.

The graph in FIG. 19 shows a total of seven particles that clearly stand out from the signal noise. It is possible that many smaller particles are subsumed by the noise. These may be taken into account with the use of the noise as an independent parameter.

Figure 20:
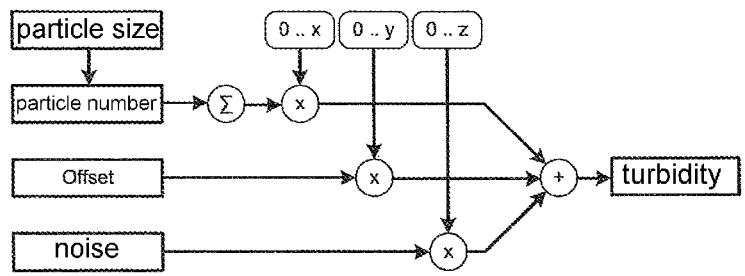
FIGS. 20 and 21: a schematic of a mathematical association between the parameters taken from the flow of data.
Figure 21:
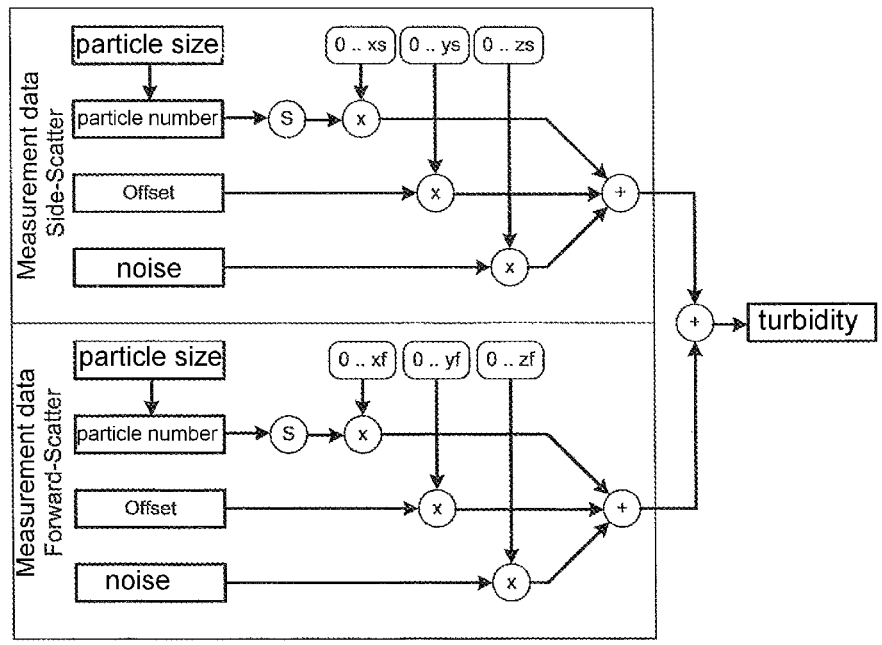

FIGS. 20 and 21 show an illustrative mathematical association between the parameters taken from the flow of data in a working example of a method of the disclosure. Parameters are weighted depending on the properties of a measurement system and a measurement transducer. It is also possible here to assign the value of zero to a weighting factor, which corresponds to effectively ignoring the corresponding parameter.

Figure 22:
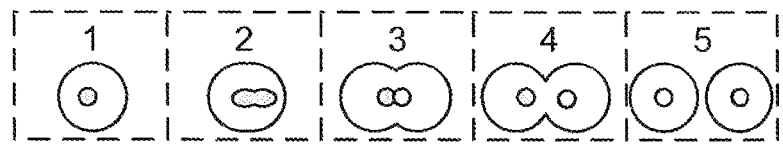
FIG. 22: a schematic of a typical cell division process.

FIG. 22 shows a schematic of a typical cell division procedure. The stations numbered 1 to 5 are described briefly below:
1: individual healthy cells with sufficient nutrients in the immediate environment;
2: cell with its cell nucleus beginning to duplicate;
3: cell with two completely formed cell nuclei, wall beginning to divide by necking;
4: cells no longer in contact, surrounding cell closes;
5: two complete and independent cells.

Figure 23:
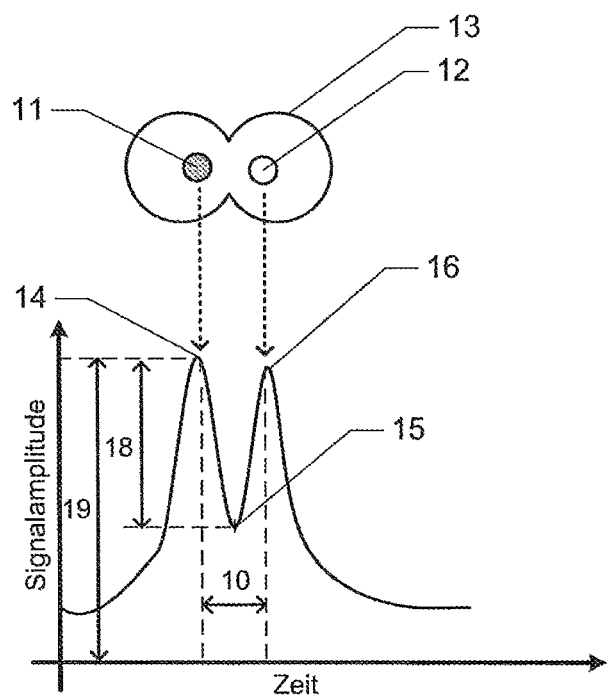
FIG. 23: a schematic of the recording of a signal shape in the scanning of a cell in the process of division.
Figure 24:
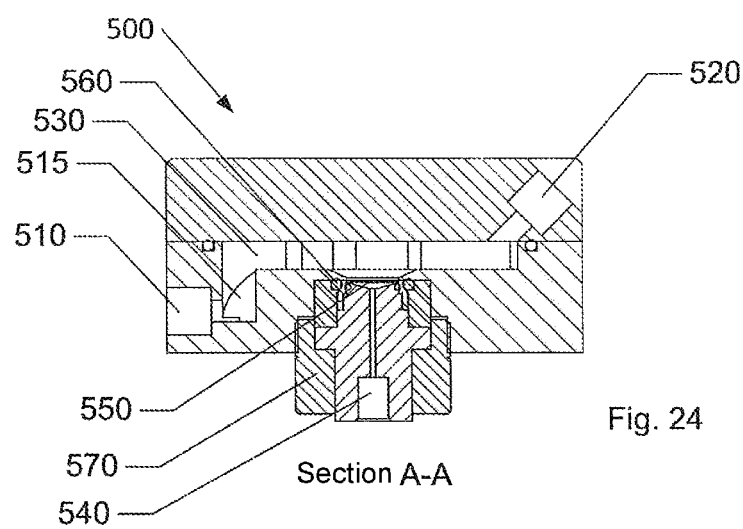
FIGS. 24 to 28: a crossflow filter.
Figure 25:
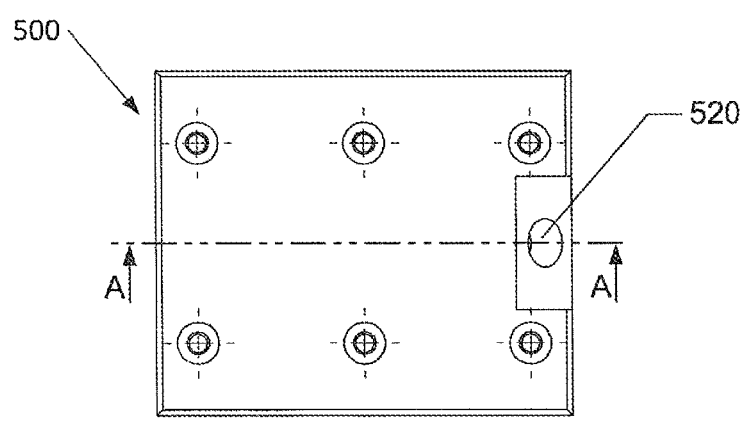
Figure 26:
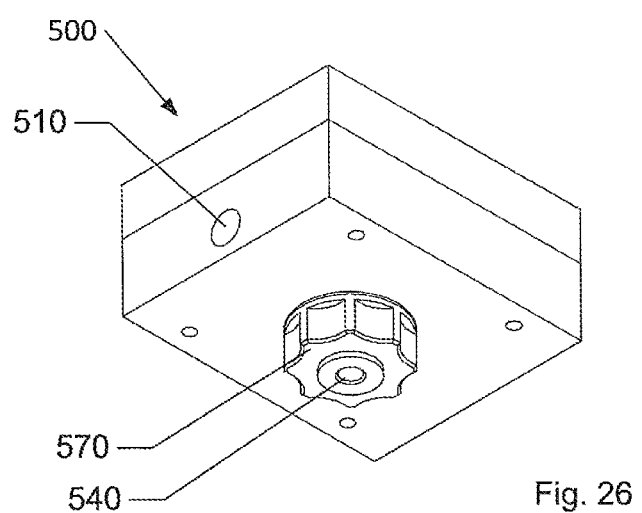
Figure 27:
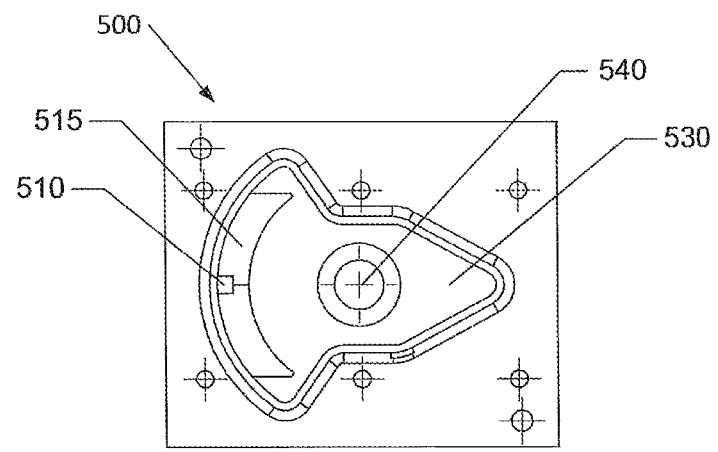
Figure 28:
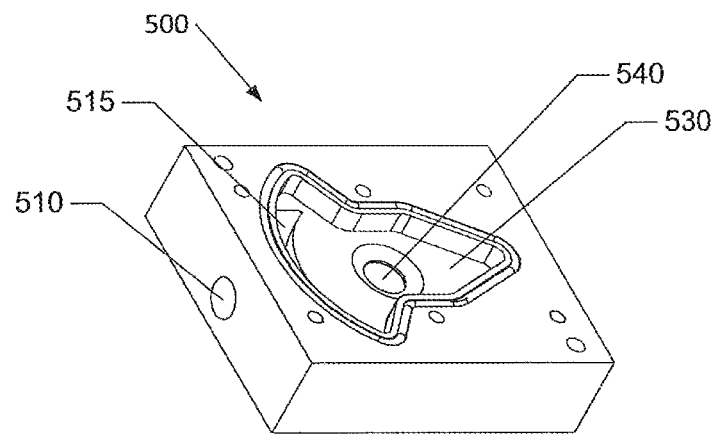
Figure 29:
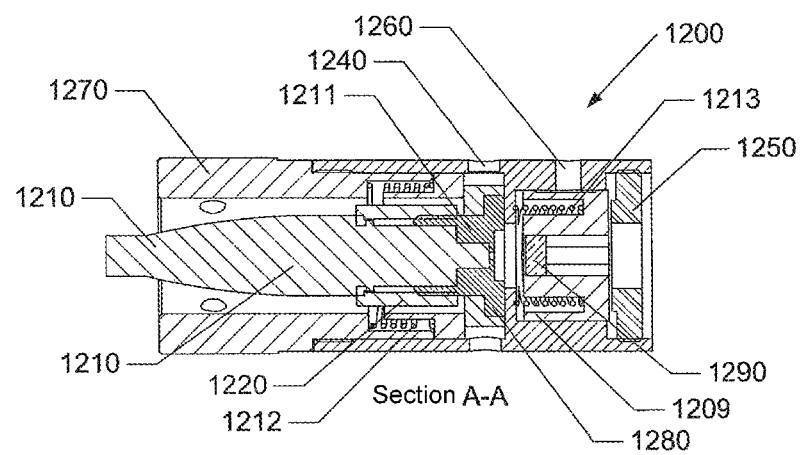
FIGS. 29 to 32: directing optics
Figure 30:
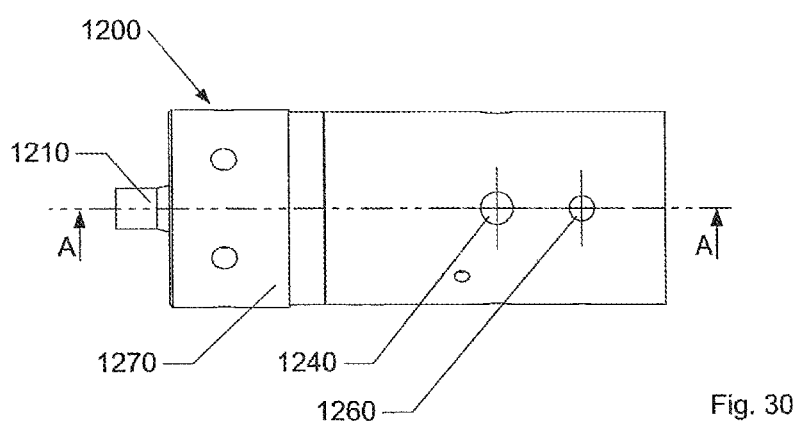
Figure 31:
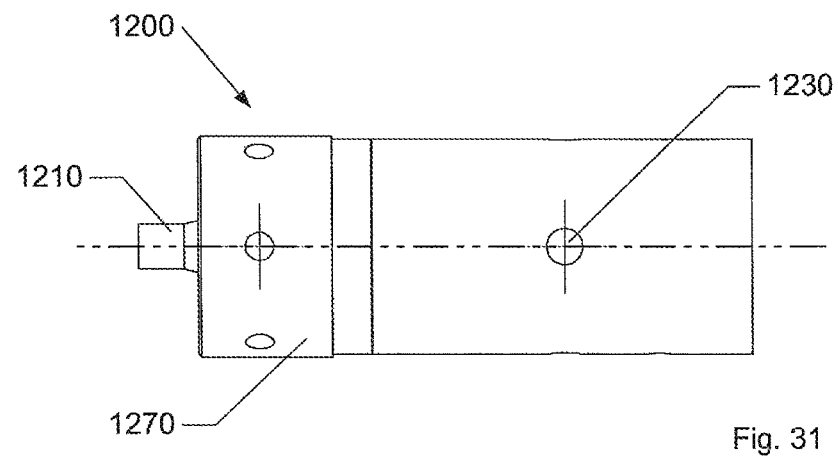
Figure 32:
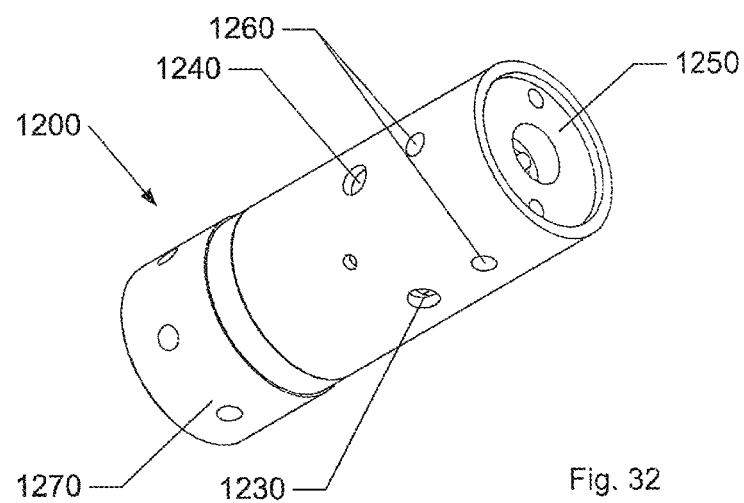

FIG. 23 shows, by way of example, recording of a signal shape on scanning of a cell in the process of division. Two cell nuclei 11, 12 are apparent here. These still have a common cell wall 13.

A first maximum 14 in the signal progression is caused by the first cell nucleus 11. A second maximum 16 is caused by the second cell nucleus 12. A minimum 15 between the two maxima 14, 16 is dependent on the distance between the two cell nuclei 11, 12.

After the second maximum 16, a flattening progression is observed. For the example presented here, it is assumed that the next pulse is sufficiently far removed for there to be no further influence at this time.

The distance between maximum and minimum is labeled by reference numeral 18. This parameter is used as input variable for the method presented here. The signal amplitude 19 at the time of the first maximum 14 can likewise be used. As an alternative, it would also be possible for this purpose to use the signal amplitude of the second maximum 16. The signal separation in time between the two cell nuclei 11, 12 is labeled by reference numeral 10. This too is an input parameter.

FIGS. 24 to 28 show a crossflow filter 500 already mentioned with regard to FIG. 1. This serves to enable bubble-free sampling of fluids in sample flow systems, which is of central significance for flow cytometry. Bubbles, including microbubbles, caused by the sampling or by the flow across sampling filters (turbulence), can lead to measurement errors. For example, scattered light effects, lateral shifts in the sample jet and, in the case of microbubbles, perturbations in the scattered light channel may be caused.

The crossflow filter 500 shown here enables extremely bubble-free obtaining of aqueous samples. By means of a specific design and the arrangement of the components described further down, especially a channel, and the inlet and outlet connection, what is achieved is that dissolved oxygen and bubbles collect at the crossflow filter and do not get into the measurement sample. Moreover, simple replacement of the filter is possible.

The crossflow filter 500 has a channel 530 having an inlet 510 and an outlet 520. A fluid, especially water from a standard drinking water supply, flows through this channel 530, with the water flowing from the inlet 510 to the outlet 520.

Adjoining the channel 530 is provided a filter 550, which is in turn connected to a sample outlet 540. The sample outlet 540 is connected to the inlet connection 110 shown in FIG. 1.

The channel 530 narrows in the region of the filter 550 from the inlet 510 toward the outlet 520. This permits an increase in the flow rate, which avoids bubble formation and enables removal of bubbles that form. The channel 530 has, at the inlet 510, an inlet funnel 515, by means of which incoming fluid is better distributed across the channel 530. This too avoids bubble formation.

The outlet 520 is oblique with respect to the channel 530, with the outlet 520 pointing upward in the installed position. This enables direct removal of bubbles upward, which do of course tend to rise upward in water.

The filter 550 is surrounded by a seal 560. This prevents leakage of the water flowing through the channel 530. The filter 530 is held by a nut 570, which can be screwed on and off in a simple manner by means of a thread (not shown). This permits reliable holding of the filter 550 and easy changing of the filter by removing the nut 570.

FIGS. 29 to 32 show the focusing optics 1200 in greater detail.

The coupling of light into the flow measurement cell 1300 is one of the core elements of flow cytometry. The more exact and defined the manner of illumination of the individual bacteria stained by fluorescent dye with the laser beam, the lower the scatter in the luminescence intensity of the bacteria. Variations in luminescence intensity have the result that the detectors do not correctly detect the bacterium since the luminescence intensity includes information about the size of the bacterium.

A homogeneous form of illumination (illumination window) horizontal, vertical (flow direction in the measurement cuvette) and in depthwise direction is a prerequisite for keeping scatter low.

Optical fiber-coupled beamformer lenses known from the prior art typically consist of a focusing lens, a beamformer element and an imaging lens. This optical setup with three optical elements is of complex construction, for instance the positioning of the lenses. Moreover, such a design requires high mechanical stability, which cannot be assured outside of defined laboratory conditions.

By means of the focusing unit 1200 presented here, precise adjustment and mechanical fixing of a laser beam at the exit of light from an optical fiber is enabled. The demands on environmental conditions are distinctly reduced as a result.

The focusing unit 1200 here comprises an optical fiber connection 1210. It also has an optical fiber connector 1220 that serves to hold the optical fiber connection 1210. The optical fiber connector 1220 can be moved in a plane transverse to the light beam by means of x positioning 1230 and y positioning 1240.

An optical element 1290 ensures the combination of the functionalities of a focusing lens, a beamformer element and an imaging lens. This is therefore a single element which is intrinsically stable and is resistant to influences such as vibrations or variations in temperature, for example. The optical element 1290 is retained by a threaded plate 1250. An optical element frame can be held in x direction by means of a cylinder screw 1260. Additionally provided is a clamp apparatus 1270, in order to ensure lateral positioning and rotation.

The optical fiber connector 1220 is held and fixed by a positioning flange 1280.

The optical element 1290 is held by an optical element frame 1209.

Additionally provided is a positioning ring 1211. By means of a compression spring 1212, movement in x direction, y direction and rotation can be assisted.

Assigned to a further compression spring 1213 in z direction is the optical element frame 1209. Also provided is a block 1260 of the optical element frame 1209 by means of two cylinder screws in z direction.

Figure 33:
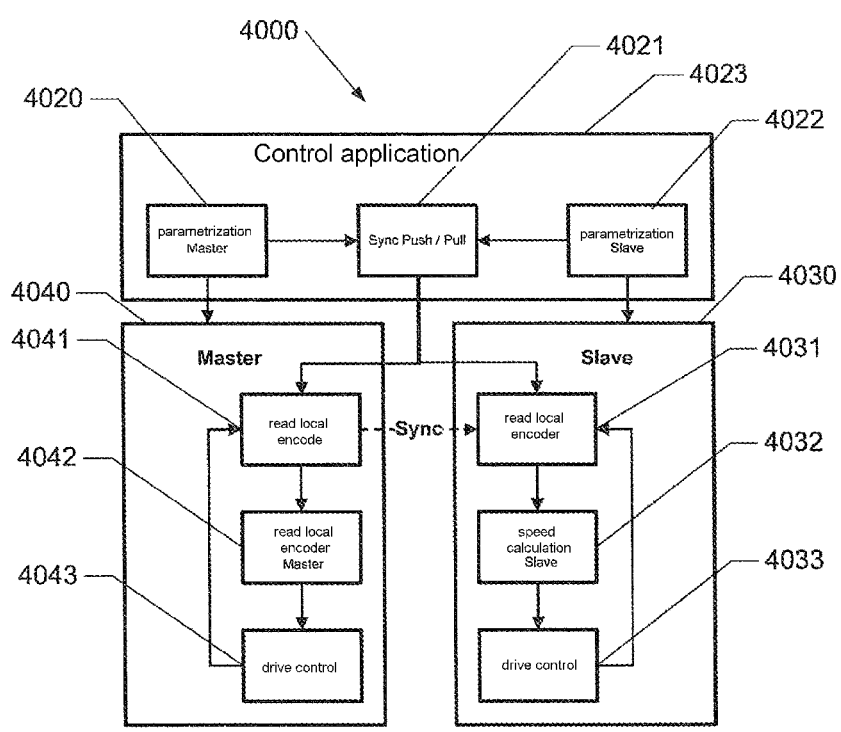
FIGS. 33 and 34: a schematic of the operation of injection units.
Figure 34:
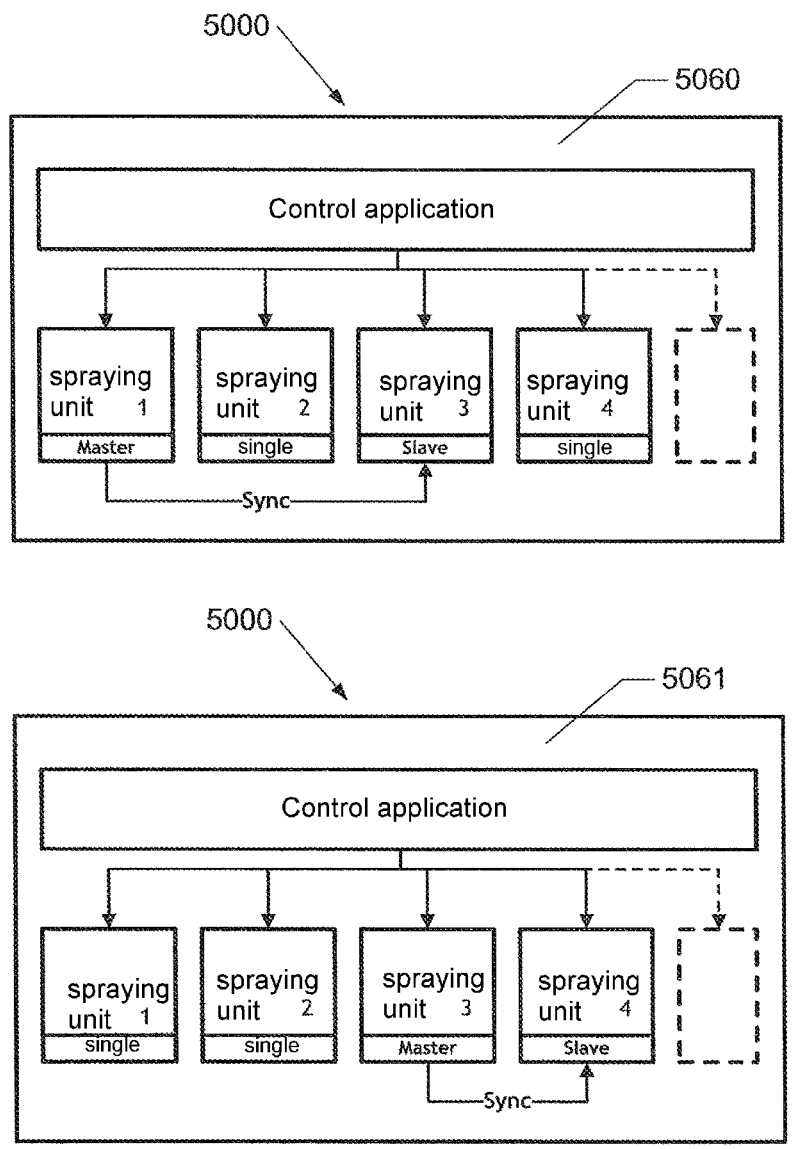
Figure 1:
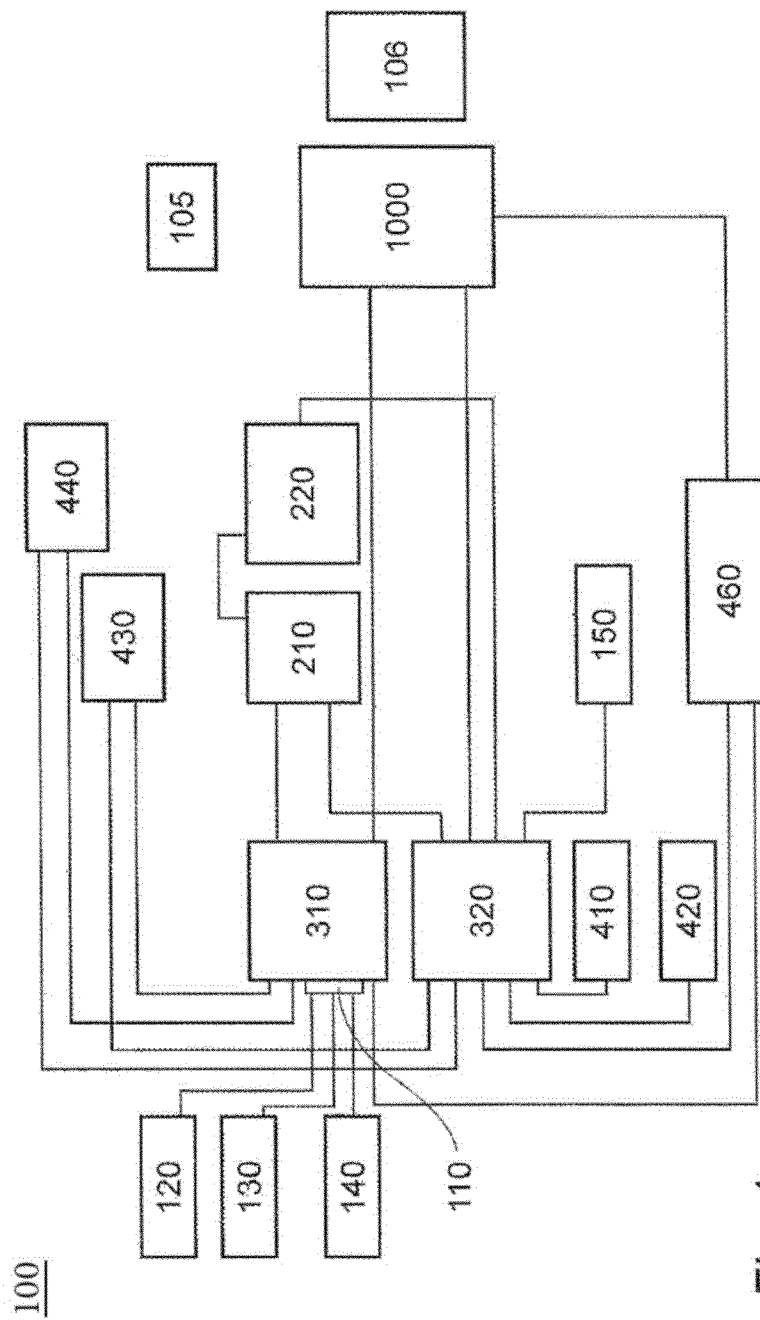

FIGS. 33 and 34 show, in schematic form, the operation of injection units in a flow cytometer of the disclosure. For this purpose, schemes 4000 and 5000 are shown.

The individual operation of an injection unit is effected by parametrization 4020 of the necessary information by a control application 4023, connected to the respective injection unit by a communication channel. Subsequently, the process (for example drawing-up and expulsion) is started by the control application (4021). The control application 4040 running in the injection unit translates the volume to a number of increments to be run in a position encoder on the injection unit. In a cyclical manner, the current value of the position encoder on the injection unit is read out (4041), the corresponding parametrized speed is calculated (4042), and then the desired speed is assigned to the motor controller (4043). This is done until the desired encoder position has been attained and hence the corresponding volume has been drawn up or expelled.

The implementation of the disclosure for the synchronous operation of two or more injection units is described hereinafter: the position encoder signal from an injection unit (master) 4040 is coupled electrically to a second or multiple injection unit(s) (slave) 4030. For the master unit 4040, the process of drawing-up and expulsion remains identical to the individual operation described. The control application 4023 parametrizes (4022) the slave units 4030 with the volume to be moved and a calculated factor which is applied to the encoder pulses of the master 4040. This factor corresponds to the ratio of the fluids depending on the injection volumes used and the total number of encoder pulses over the complete injection length. In addition, the slave unit 4030 is set to a mode that puts the control application on the slave 4030 in the state in which primarily the pulses from the master encoder are used.

The control application 4023 starts the synchronous process 21 on the master 4040. The slave 4030 cyclically reads out the encoder pulses from the master (4031), uses the pulses and the parametrized factor to calculate a rolling average speed (4032), and assigns this to the motor controller (4033). Since the number of increments to be run by the slave 4030 has been parametrized beforehand, there is additionally constant verification of whether the final position has nearly been attained, i.e. it is within a defined number of increments from the target. If this is the case, from this time, it is no longer the master encoder that is evaluated but rather the current slave's own positional encoder in order to achieve the final position. The process is complete when both injection units have reached their final encoder position.

By virtue of the parametrization of the control application, it is possible to operate an injection unit either on its own or in synchronous integration, and it may be either master or slave in the case of synchronous operation. By way of example, four injection units are actuated in one process step (5060). Injection units two and four are in individual operation in this process step. Injection units one and three are parametrized for synchronous operation, with injection unit one functioning as master and injection unit three following the master as slave. In a subsequent process step (5061) with physically identical construction, the injection units are then configured in such a way that injection unit three that formerly operated as slave now functions as master for injection unit four.

It should be mentioned that scanning of signal pulses by the detectors mentioned further up can preferably be effected with 20 to 60 scans per signal pulse. This enables exact recognition of the pulse shape. For this purpose, for example, scanning is effected with a resolution between 2 megasamples per second and 4 megasamples per second.

Correspondingly, an analog-digital converter (ADC) is preferably formed. This may have, for example, a sampling rate between 2 and 4 megasamples per second. Preference is given to a signal resolution of 24 bits.

There follows a structured recitation of possible features that may be of inventive relevance:

1. Flow cytometer characterized by a design as a compact measurement device suitable for industry.
2. Flow cytometer according to feature 1, wherein automated performance of all measurement steps is envisaged.
3. Apparatus for synchronous operation of injection units, comprising two or more electrically coupled and motor-driven injection units, especially for use in a flow cytometer according to either of the preceding features.
4. Detection unit characterized by an optics monoblock for arrangement of the elements of the detection unit, especially for use in a flow cytometer according to any of the preceding claims.
5. Double-slit stray light stop, especially for use in a detection unit according to feature 4, preferably in a flow cytometer according to any of the preceding claims.
6. Light source comprising a laser with integrated fiber coupling, especially for use in a detection unit according to feature 4, preferably in a flow cytometer according to any of the preceding features.
7. Flow measurement cell unit, especially for use in a detection unit according to feature 4, preferably in a flow cytometer according to any of the preceding features.
8. Method of measuring microbiological and physical sample parameters and subsequent data evaluation with a flow cytometer according to any of the preceding features.
9. Method of evaluating flow cytometry scatter channel measurement data, preferably for determining the turbidity of fluids.
10. Method of recognizing cells in the state of cell division on evaluation of flow cytometry measurement data.

The claims now being filed with the application and filed at a later stage are without prejudice for the achievement of further protection.

If it should be found on closer examination, especially of the relevant prior art, that one feature or another is favorable but not of crucial importance for the aim of the invention, a formulation that no longer includes such a feature, especially in the main claim, is of course desired even now. Such a sub-combination is also covered by the disclosure of this application.

It should further be noted that the configurations and variants of the invention that are described in the different embodiments and shown in the figures are combinable with one another as desired. In this context, individual or multiple features are mutually exchangeable as desired. These combinations of features are likewise disclosed as well.

The dependency relationships cited in the dependent claims indicate the further development of the subject matter of the main claim by the features of the respective subsidiary claim. However, these should not be regarded as a disclaimer of the achievement of independent product protection for the features of the subsidiary claims having the dependency references.

Features that have been disclosed only in the description or else individual features from claims comprising a multitude of features can be adopted into the claim or the independent claims at any time as having significance essential to the invention for delimitation from the prior art, even when such features have been mentioned in association with other features or achieve particularly favorable results in association with other features.

All the features and advantages, including structural details, spatial arrangements and method steps, which follow from the claims, the description and the drawing can be fundamental to the invention both on their own and in different combinations. It is to be understood that the foregoing is a description of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

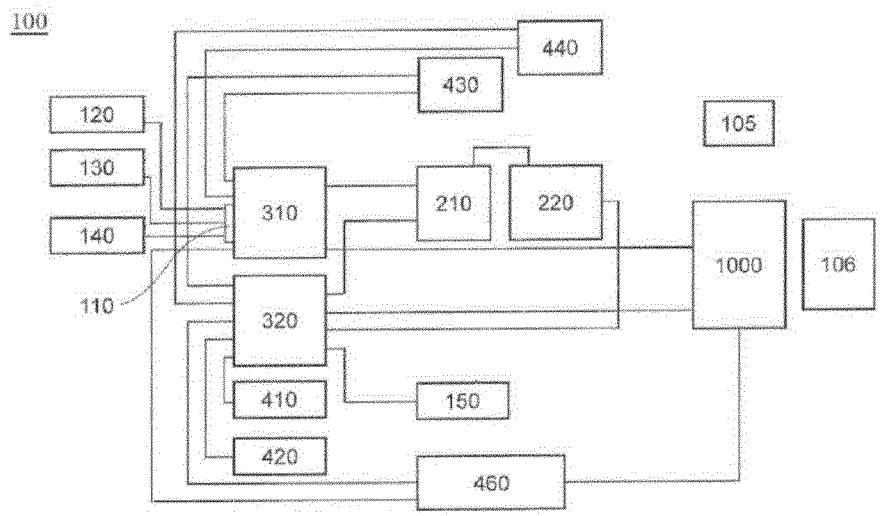

The invention claimed is:

1. A flow cytometer arrangement comprising:
   a flow measurement cell,
   a mixer,
   first pump and a second pump,
   an inlet connection,
   a dye reservoir, and
   a sheath fluid reservoir,
   wherein the first pump is connected on an inlet side to the inlet connection for suction of sample fluid,
   wherein the second pump is connected on the inlet side to the dye reservoir for suction of dye,
   wherein the first pump and the second pump are connected on an outlet side to the mixer, in order to pump sample fluid and dye into the mixer, and the mixer is configured to mix the sample fluid and the dye to give a mixture,
   wherein the second pump is connected on the inlet side to the mixer for suction of the mixture,
   wherein the first pump is connected on the inlet side to the sheath fluid reservoir for suction of sheath fluid,
   wherein the second pump is connected on the outlet side to the flow measurement cell in order to produce a sample jet through the flow measurement cell from the mixture, and
   wherein the first pump is connected on the outlet side to the flow measurement cell in order to produce a sheath jet through the flow measurement cell that ensheaths the sample jet from the sheath fluid.

2. The flow cytometer arrangement as claimed in claim 1 wherein:
   the mixer is connected on the outlet side to an incubator which is connected on the outlet side to the second pump.

3. The flow cytometer arrangement as claimed in claim 1 wherein:
   the first pump is configured to suck in a defined first volume of sample fluid from the inlet connection,
   the second pump is configured to suck in a defined second volume of dye from the dye reservoir, and
   the first pump and the second pump are configured to pump the first volume of sample fluid and the second volume of dye, after the time of suction, simultaneously into the mixer.

4. The flow cytometer arrangement as claimed in claim 1 wherein:
   the pumps are in the form of spindle-actuated piston pumps.

5. The flow cytometer arrangement as claimed in claim 1 wherein:
   the flow cytometer arrangement comprises a detector arrangement which in turn comprises the following:
   a laser configured to produce a laser beam,
   directing optics configured to direct the laser beam toward the flow measurement cell,
   a number of detectors configured to detect the laser beam that has passed through the flow measurement cell.

6. The flow cytometer arrangement as claimed in claim 1 wherein:
   the flow cytometer arrangement comprises a control device configured to control the pumps.

7. The flow cytometer arrangement as claimed in claim 6, wherein:
   the control device is configured to control the first pump and the second pump in such a way that they simultaneously pump defined volumes of sample fluid and dye into the mixer.

8. The flow cytometer arrangement as claimed in claim 6 wherein:
   the control device is configured to control the second pump in such a way that the second pump sucks mixture out of the mixer or an incubator.

9. The flow cytometer arrangement as claimed in claim 8, wherein:
   the control device is configured first to trigger the pumping of sample fluid and dye into the mixer, then to wait for a predetermined incubation time, and then to trigger the suction of the mixture.

10. The flow cytometer arrangement as claimed in claim 6 wherein:
    the control device is configured to control the first pump such that it pumps sheath fluid into the flow measurement cell, and simultaneously to control the second pump such that it pumps mixture sucked in from the mixer or an incubator into the flow measurement cell.

* * * * *

UNITED STATES PATENT AND TRADEMARK OFFICE
CERTIFICATE OF CORRECTION

| | |
|---|---|
| PATENT NO. | : 11,300,495 B2 |
| APPLICATION NO. | : 16/767467 |
| DATED | : April 12, 2022 |
| INVENTOR(S) | : Martin Kuhn |

It is certified that error appears in the above-identified patent and that said Letters Patent is hereby corrected as shown below:

On the Title Page

The Title Page, showing an illustrative figure, should be deleted and substitute therefor the attached title page.

In the Drawings

Please replace Fig. 1 with Fig. 1 as shown on the attached page.

Signed and Sealed this
Eighth Day of November, 2022

Katherine Kelly Vidal
*Director of the United States Patent and Trademark Office*

(12) United States Patent
Kuhn

(10) Patent No.: US 11,300,495 B2
(45) Date of Patent: Apr. 12, 2022

(54) FLOW CYTOMETER ARRANGEMENT

(71) Applicant: Martin Kuhn, Glattfelden (CH)

(72) Inventor: Martin Kuhn, Glattfelden (CH)

(73) Assignee: Martin Kuhn, Glattfelden (CH)

(*) Notice: Subject to any disclaimer, the term of this patent is extended or adjusted under 35 U.S.C. 154(b) by 125 days.

(21) Appl. No.: 16/767,467

(22) PCT Filed: Nov. 27, 2018

(86) PCT No.: PCT/EP2018/082712
§ 371 (c)(1),
(2) Date: May 27, 2020

(87) PCT Pub. No.: WO2019/102038
PCT Pub. Date: May 31, 2019

(65) Prior Publication Data
US 2020/0371013 A1    Nov. 26, 2020

(30) Foreign Application Priority Data
Nov. 27, 2017   (DE) .................. 102017128029.4

(51) Int. Cl.
*G01N 1/14*    (2006.01)
*G01N 15/14*    (2006.01)
(Continued)

(52) U.S. Cl.
CPC ........... *G01N 15/1434* (2013.01); *G01N 1/14* (2013.01); *G01N 1/31* (2013.01); *G01N 1/38* (2013.01); *G01N 15/1404* (2013.01); *G01N 33/18* (2013.01); *G01N 2015/0088* (2013.01); *G01N 2015/1006* (2013.01); *G01N 2015/1409* (2013.01); *G01N 2015/1413* (2013.01); *G01N 2015/1486* (2013.01)

(58) Field of Classification Search
CPC ........ G01N 15/1434; G01N 1/14; G01N 1/31; G01N 1/38; G01N 15/1404; G01N 33/18; G01N 2015/0088; G01N 2015/1006; G01N 2015/1409; G01N 2015/1413; G01N 2015/1486
See application file for complete search history.

(56) References Cited

U.S. PATENT DOCUMENTS 4,695,431 A * 9/1987 Farrell .............. G01N 35/1095
417/267
5,978,435 A * 11/1999 Christensen ....... G01N 15/1456
377/10
(Continued)

FOREIGN PATENT DOCUMENTS

EP    0634640 A1    1/1995
WO    9707390 A1    2/1997

OTHER PUBLICATIONS

International Preliminary Report on Patentability for International Application No. PCT/EP2018/082712 dated Jun. 2, 2020 (7 pages).
(Continued)

*Primary Examiner* — Roy M Punnoose
(74) *Attorney, Agent, or Firm* — Reising Ethington, P.C.

(57) ABSTRACT

The disclosure relates to a flow cytometer arrangement, in which a sample is mixed with a colorant by means of two pumps and the mixture is introduced together with a sheath flow into a flow cell.

10 Claims, 21 Drawing Sheets